United States Patent
Bolduc et al.

(10) Patent No.: US 6,622,367 B1
(45) Date of Patent: Sep. 23, 2003

(54) INTRAVASCULAR DEVICE AND METHOD OF MANUFACTURE AND USE

(75) Inventors: Lee R. Bolduc, Mountain View, CA (US); Gilbert S. Laroya, Santa Clara, CA (US); B. Douglas Lewis, Stanford, CA (US)

(73) Assignee: Salient Interventional Systems, Inc., Cupertino, CA (US)

( * ) Notice: Subject to any disclaimer, the term of this patent is extended or adjusted under 35 U.S.C. 154(b) by 0 days.

(21) Appl. No.: 09/434,390

(22) Filed: Nov. 4, 1999

Related U.S. Application Data

(63) Continuation-in-part of application No. 09/311,903, filed on May 14, 1999, now Pat. No. 6,295,990, which is a continuation-in-part of application No. 09/243,578, filed on Feb. 3, 1999, now abandoned, which is a continuation-in-part of application No. 09/018,214, filed on Feb. 3, 1998, now Pat. No. 6,044,845.

(51) Int. Cl.[7] ................................................. B23P 11/02
(52) U.S. Cl. ......................... 29/447; 29/458; 29/469.5; 604/8
(58) Field of Search ....................... 29/447, 458, 527.2, 29/469.5, 423; 128/898; 604/8, 9

(56) References Cited

U.S. PATENT DOCUMENTS

| | | | |
|---|---|---|---|
| 1,982,852 A | * 12/1934 | Bergstrom et al. ............ 29/447 |
| 3,081,495 A | * 3/1963 | Kovatch ....................... 29/423 |
| 3,297,819 A | * 1/1967 | Wetmore ....................... 29/447 |
| 3,579,822 A | * 5/1971 | Dietrich ....................... 29/423 |
| 3,882,590 A | * 5/1975 | Mazelsky ...................... 29/447 |
| 3,989,602 A | * 11/1976 | McCandless et al. ........ 29/527.2 |
| 4,103,689 A | 8/1978 | Leighton |
| 4,221,457 A | * 9/1980 | Allen et al. ................... 29/447 |
| 4,468,216 A | 8/1984 | Muto |
| 4,564,014 A | 1/1986 | Fogarty et al. |
| 4,661,094 A | 4/1987 | Simpson |
| 4,666,426 A | 5/1987 | Aigner |
| 4,698,890 A | * 10/1987 | Neaves ....................... 29/469.5 |
| 4,804,358 A | 2/1989 | Karcher et al. |
| 4,846,174 A | 7/1989 | Willard et al. |
| 4,850,969 A | 7/1989 | Jackson |
| 4,873,978 A | 10/1989 | Ginsburg |
| 4,921,478 A | 5/1990 | Solano et al. |
| 4,921,483 A | 5/1990 | Wijay et al. |
| 4,926,858 A | 5/1990 | Gifford et al. |

(List continued on next page.)

FOREIGN PATENT DOCUMENTS

| | | |
|---|---|---|
| CA | CA 1322315 | 9/1993 |
| DE | 3731590 | 7/1988 |
| DE | 3731590 C1 | 7/1988 |
| EP | 0476796 B1 | 3/1992 |
| EP | 0476796 | 3/1992 |
| EP | 0476796 A1 | 3/1992 |
| WO | WO 83/01893 | 6/1983 |
| WO | WO 88/06865 | 9/1988 |
| WO | WO 92/20398 | 11/1992 |
| WO | WO 97/19713 | 6/1997 |
| WO | WO 97/49447 | 12/1997 |
| WO | WO 00/13734 | 3/2000 |

Primary Examiner—Gregory M. Vidovich
Assistant Examiner—Jermie E. Cozart
(74) Attorney, Agent, or Firm—Hoekendijk & Lynch, LLP; Jens E. Hoekendijk

(57) ABSTRACT

An intravascular device and method of constructing an intravascular device. The device has a proximal portion which is stiffer than a distal portion. The device of the present invention may also be advanced through small vessels without the aid of a guidewire although a guidewire may be used when necessary. The device may be manufactured in a number of different ways and a preferred method is to use an expanded PTFE liner at the distal portion and an etched PTFE liner along the proximal portion. The device also has a number of different jacket sections, preferably at least four, with increasing durometer towards the proximal end and a braided section with varying pic along the length.

20 Claims, 25 Drawing Sheets

U.S. PATENT DOCUMENTS

| | | | |
|---|---|---|---|
| 5,005,755 A | * 4/1991 | Takahashi et al. | 29/469.5 |
| 5,011,468 A | 4/1991 | Lundquist et al. | |
| 5,011,469 A | 4/1991 | Buckberg et al. | |
| 5,066,282 A | 11/1991 | Wijay et al. | |
| 5,090,960 A | 2/1992 | Don Michael | |
| 5,106,363 A | 4/1992 | Nobuyoshi | |
| 5,147,315 A | * 9/1992 | Weber | 604/164 |
| 5,149,321 A | 9/1992 | Klatz et al. | |
| 5,158,540 A | 10/1992 | Wijay et al. | |
| 5,180,387 A | 1/1993 | Ghajar et al. | |
| 5,184,627 A | 2/1993 | de Toledo | |
| 5,186,713 A | 2/1993 | Raible | |
| 5,250,034 A | 10/1993 | Appling et al. | |
| 5,341,555 A | * 8/1994 | Warden et al. | 29/469.5 |
| 5,364,344 A | 11/1994 | Beattie et al. | |
| 5,403,274 A | 4/1995 | Cannon | |
| 5,405,322 A | 4/1995 | Lennox et al. | |
| 5,407,424 A | 4/1995 | LaFontaine et al. | |
| 5,425,723 A | 6/1995 | Wang | |
| 5,445,624 A | 8/1995 | Jimenez | |
| 5,451,207 A | 9/1995 | Yock | |
| 5,462,523 A | 10/1995 | Samson et al. | |
| 5,496,294 A | 3/1996 | Hergenrother et al. | |
| 5,505,710 A | 4/1996 | Dorsey, III | |
| 5,531,715 A | 7/1996 | Engelson et al. | |
| 5,533,957 A | 7/1996 | Aldea | |
| 5,571,086 A | 11/1996 | Kaplan et al. | |
| 5,584,803 A | 12/1996 | Stevens et al. | |
| 5,584,804 A | 12/1996 | Klatz et al. | |
| 5,601,538 A | 2/1997 | Deem | |
| 5,607,478 A | * 3/1997 | Lentz et al. | 623/12 |
| 5,624,396 A | 4/1997 | McNamara et al. | |
| 5,624,397 A | * 4/1997 | Snoke et al. | 604/95 |
| 5,626,564 A | 5/1997 | Zhan et al. | |
| 5,643,228 A | 7/1997 | Schucart et al. | |
| 5,693,017 A | 12/1997 | Spears et al. | |
| 5,713,847 A | 2/1998 | Howard, III et al. | |
| 5,716,318 A | 2/1998 | Manning | |
| 5,738,649 A | 4/1998 | Macoviak | |
| 5,782,797 A | 7/1998 | Schweich, Jr. et al. | |
| 5,791,036 A | * 8/1998 | Goodin et al. | 29/423 |
| 5,794,629 A | 8/1998 | Frazee | |
| 5,797,876 A | 8/1998 | Spears et al. | |
| 5,827,242 A | 10/1998 | Follmer et al. | |
| 5,833,650 A | 11/1998 | Imran | |
| 5,865,789 A | 2/1999 | Hattler | |
| 5,879,316 A | 3/1999 | Safar et al. | |
| 5,899,890 A | 5/1999 | Chiang et al. | |
| 5,908,407 A | 6/1999 | Frazee et al. | |
| 5,925,075 A | * 7/1999 | Myers et al. | 623/1 |
| 5,957,879 A | 9/1999 | Roberts et al. | |
| 5,957,899 A | 9/1999 | Spears et al. | |
| 5,961,481 A | 10/1999 | Sterman et al. | |
| 6,027,476 A | 2/2000 | Sterman et al. | |
| 6,027,811 A | * 2/2000 | Campbell et al. | 428/411.1 |
| 6,029,671 A | 2/2000 | Stevens et al. | |
| 6,044,845 A | 4/2000 | Lewis | |
| 6,048,333 A | 4/2000 | Lennox et al. | |
| 6,071,271 A | 6/2000 | Baker et al. | |
| 6,083,198 A | 7/2000 | Afzal | |
| 6,139,517 A | 10/2000 | Macoviak et al. | |
| 6,295,990 B1 | 10/2001 | Lewis et al. | |

* cited by examiner

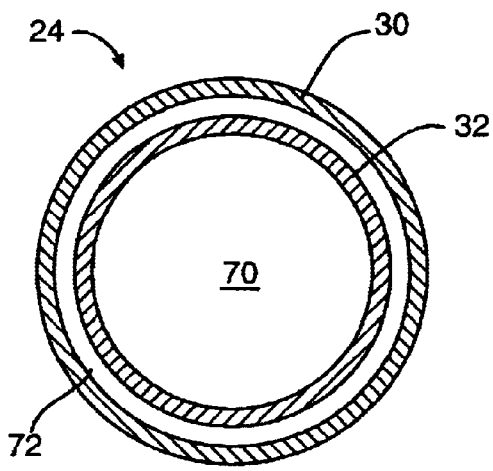
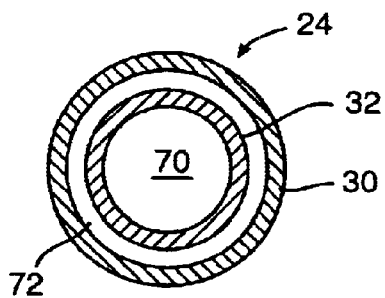
FIG. 3          FIG. 4
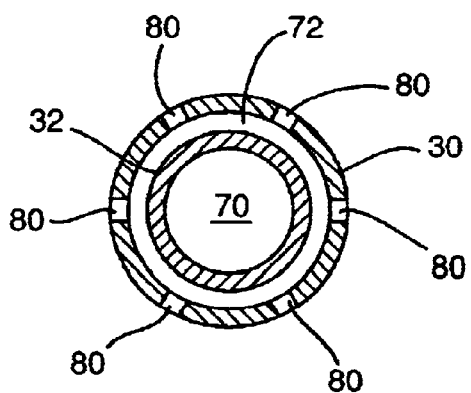
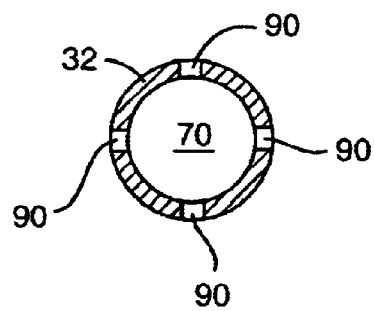
FIG. 5          FIG. 6

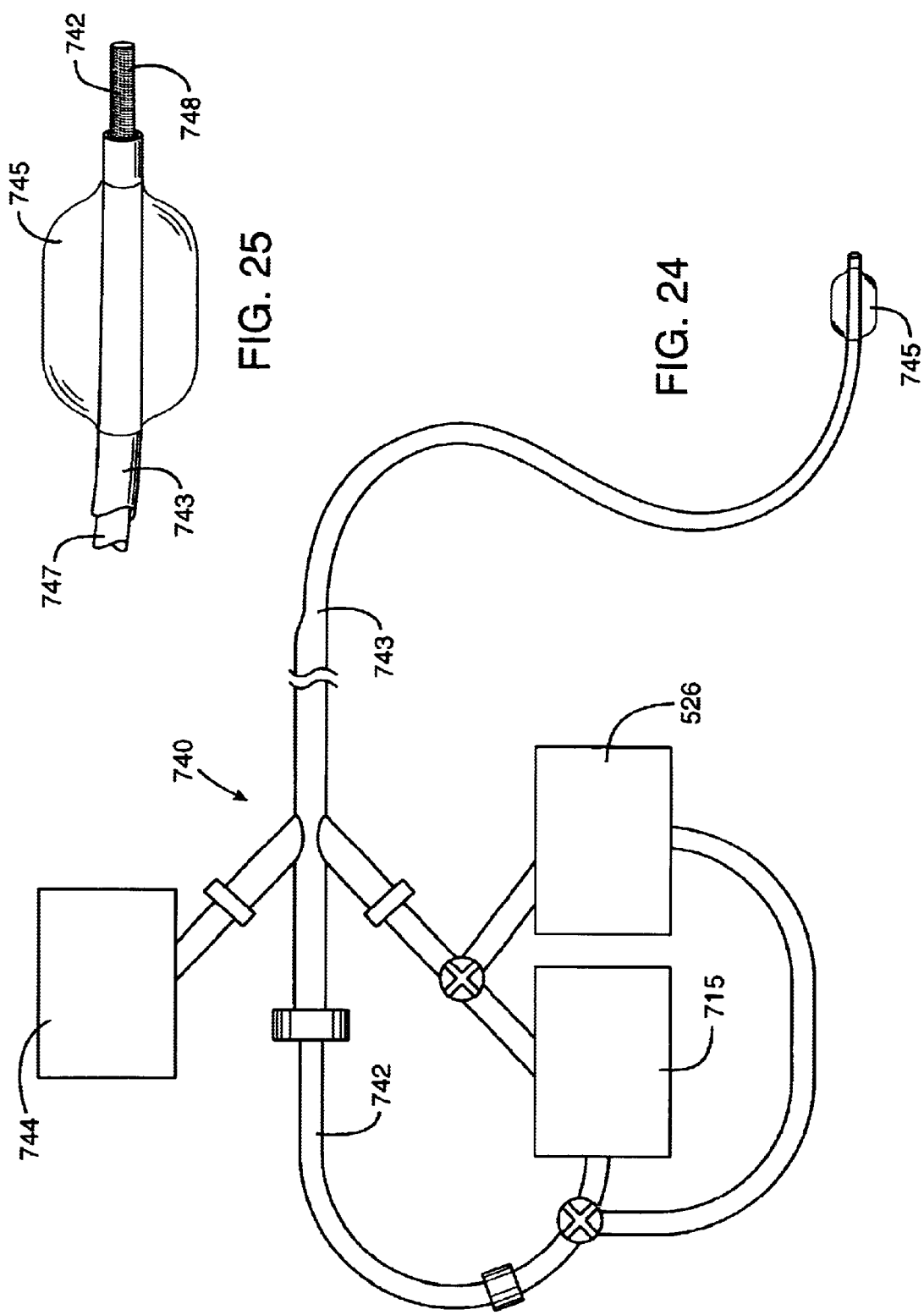

INTRAVASCULAR DEVICE AND METHOD OF MANUFACTURE AND USE

CROSS-REFERENCES TO RELATED APPLICATIONS

The present application is a continuation-in-part of application Ser. No. 09/311,903, filed May 14, 1999 now U.S. Pat. No. 6,295,990, which is a continuation-in-part of application Ser. No. 09/243,578, filed Feb. 3, 1999 now abandoned, which is a continuation-in-part of application Ser. No. 09/018,214, filed of Feb. 3, 1998 now U.S. Pat. No. 6,044,845, the full disclosures of which are incorporated herein by reference.

BACKGROUND OF THE INVENTION

The present invention relates generally to intravascular devices and methods. Intravascular devices are used to access various areas of the vasculature for a variety of reasons. Such devices are used to deliver and withdraw fluids and to deliver other devices such as stents, angioplasty balloons and thrombolytic devices.

A specific application of the present invention is for treating acute arterial ischemia in areas such as the brain. The devices and methods of the present invention are particularly useful in connection with the devices and methods described in U.S. patent application Ser. No. 09/311,903, filed May 14, 1999 now U.S. Pat. No. 6,295,990 by Lewis and Bolduc which describe devices for treating acute ischemia. The invention may, of course, be used in other locations in the body for any other purpose.

SUMMARY OF THE INVENTION

The present invention is directed to intravascular devices and methods of construction. As an example of a use of the present invention, methods and devices for treating ischemia resulting from the partial or total obstruction of a blood vessel are described. Usually, the obstructions will be high-grade blockages, e.g., those which result in greater than 75% flow reduction, but in some instances they may be of a lower grade, e.g., ulcerated lesions. As used hereinafter, the terms "obstruction," "occlusion," and "blockage" will be used generally interchangeably and will refer to both total obstructions where substantially all flow through a blood vessel is stopped as well as to partial obstructions where flow through the blood vessel remains, although at a lower rate than if the obstruction were absent.

Preferred use of the present invention is for the treatment of patients suffering from acute stroke resulting from a sudden, catastrophic blockage of a cerebral artery. The invention may also be used to minimize or prevent ischemia during other conditions which result in blocked points or segments in the cerebral arterial vasculature, such as iatrogenic occlusion of an artery, e.g., during neurosurgery, or to relieve vasospasm induced ischemia. The present invention, however, will also be useful for treating acute blockages in other portions of the vasculature as well as for treating chronic occlusions in the cerebral, cardiac, peripheral, mesenteric and other vasculature. Optionally, the methods of the present invention may be used to facilitate dissolving or removing the primary obstruction responsible for the ischemia, e.g., by drug delivery, mechanical intervention, or the like, while perfusion is maintained to relieve the ischemia.

Methods according to the present invention comprise penetrating a perfusion conduit through the blockage and subsequently pumping an oxygenated medium through the conduit at a rate or pressure sufficient to relieve ischemia downstream from the blockage. The oxygenated medium is preferably blood taken from the patient being treated. In some instances, however, it will be possible to use other oxygenated media, such as perfluorocarbons or other synthetic blood substitutes. In a preferred aspect of the present invention, the pumping step comprises drawing oxygenated blood from the patient, and pumping the blood back through the conduit at a controlled pressure and/or rate, typically a pressure within the range from 50 mmHg to 400 mmHg, preferably at a mean arterial pressure in the range from 50 mmHg to 150 mmHg, and at a rate in the range from 30 cc/min to 360 cc/min, usually from 30 cc/min to 240 cc/min, and preferably from 30 cc/min to 180 cc/min, for the cerebral vasculature. Usually, pressure and flow rate will both be monitored. The blood flow system preferably keeps the pressure at or below 400 mmHg, 350 mmHg, or 300 mmHg. Pressure is preferably monitored using one or more pressure sensing element(s) on the catheter which may be disposed distal and/or proximal to the obstruction where the blood or other oxygenated medium is being released. Flow rate may easily be monitored on the pumping unit in a conventional manner or may be monitored by a separate control unit. Conveniently, the blood may be withdrawn through a sheath which is used for percutaneously introducing the perfusion conduit.

It will usually be desirable to control the pressure and/or flow rate of the oxygenated medium being delivered distally to the occlusion. Usually, the delivered pressure of the oxygenated medium should be maintained below the local peak systolic pressure and/or mean arterial blood pressure of the vasculature at a location proximal to the occlusion. It will generally be undesirable to expose the vasculature distal to the occlusion to a pressure above that to which it has been exposed prior to the occlusion. Pressure control of the delivered oxygenated medium will, of course, depend on the manner in which the medium is being delivered. In instances where the oxygenated medium is blood which is being passively perfused past the occlusion, the delivered pressure will be limited to well below the inlet pressure, which is typically the local pressure in the artery immediately proximal to the occlusion. Pressure control may be necessary, however, when the oxygenated medium or blood is being actively pumped. In such cases, the pump may have a generally continuous (non-pulsatile) output or in some cases may have a pulsatile output, e.g., being pulsed to mimic coronary output. In the case of a continuous pump output, it is preferred that the pressure in the vascular bed immediately distal to the occlusion be maintained below the mean arterial pressure usually being below 150 mmHg, often being below 100 mmHg. In the case of a pulsatile pump output, the peak pressure should be maintained below the peak systolic pressure upstream of the occlusion, typically being below 200 mmHg, usually being below 150 mmHg.

Pressure control of the oxygenated medium being delivered downstream of the occlusion is preferably achieved using a digital or analog feedback control apparatus where the pressure and/or flow output of the pump is regulated based on a measured pressure and/or flow value. The pressure value may be measured directly or indirectly. For example, the pressure downstream of the occlusion may be measured indirectly through the perfusion conduit. A separate pressure lumen may be provided in the perfusion conduit and a pressure measurement transducer located at the proximal end of the conduit. Pressure sensed by a distal port of the pressure measuring conduit will then be transmitted through the conduit to the transducer. Pressure transducers are a preferred pressure sensor for measuring pressure in the vasculature distal to the occlusion. The pressure sensors may be mounted near the distal tip of the perfusion conduit itself or could be mounted on a separate guidewire or other structure which crosses the occlusion with the perfusion conduit. The pressure signals generated by the transducers are transmitted through electrically conductive elements, such as wires, to the proximal end of the perfusion conduit where they are connected to a pressure monitor connected to or integral with the controller. The pump output can then be controlled based on conventional control algorithms, such as proportional control algorithms, derivative control algorithms, integral control algorithms, or combinations thereof. In one embodiment of the present invention, the pressure sensor is spaced from the perfusion outlets so that fluid flow forces do not affect the pressure measurements.

Actual manipulation of the pressure and/or flow provided by a circulating pump can be effected in a variety of ways. In the case of centrifugal pumps, the flow can be measured at the pump output and the pressure can be measured in any of the ways set forth above. Control of both the flow rate and the pressure can be achieved by appropriately changing the pump speed and downstream flow resistance, where the latter can be manipulated using a control valve. Suitable flow control algorithms are well described in the patent and technical literature.

Control of peristaltic and other positive displacement pumps is achieved in a slightly different way. Flow volume from a positive displacement pump is a linear function of the pump speed and thus may be controlled simply by varying the pump speed. Pressure output from the positive displacement pump, in contrast, will be dependent on flow resistance downstream from the pump. In order to provide for control of the output pressure from the pump (which is necessary to control the pressure downstream of the occlusion), a pressure control system may be provided. Typically, the pressure control system may comprise a by-pass flow loop from the pump output back to the pump inlet. By then controlling the amount of blood output which is by-passed back to the inlet, that pressure can be manipulated. Typically, a flow control valve can be used to adjust the by-pass flow in order to achieve the target pressure control point downstream of the obstruction. Suitable flow and pressure control algorithms for positive displacement pumps, such as roller pumps, are well described in the patent and technical literature.

In addition to controlling pressure and/or flow rates, the systems of the present invention can provide control for a number of other parameters, such as partial oxygen pressure (pO2) in the perfused blood, partial carbon dioxide pressure (pCO2) in the perfused blood, pH in the perfused blood, temperature of the perfused blood, metabolite concentrations, and the like. Both pO2 and pCO2 can be controlled using the oxygenator in the system, as described in more detail below. The pH can be controlled by introducing appropriate physiologically acceptable pH modifier (s), such as buffer and bicarbonate solutions and the like. Temperature is controlled by providing appropriate heat exchange capabilities in the extracorporeal pumping system. The temperature will usually be decreased in order to further inhibit tissue damage from the ischemic conditions, but could be elevated for other purposes. Suitable sensors and devices for measuring each of the parameters are commercially available, and suitable control systems can be provided as separate analog units or as part of a digital controller for the entire system, such as a desk or lap top computer which is specially programmed to handle the monitoring and control functions as described in this application. Concentration and/or physiologic activity of certain formed cellular elements, such as white blood cell or platelets, can be selectively controlled with suitable control systems and devices.

A particular advantage of the present invention lies in the ability to lessen or eliminate reperfusion injury which can result from the rapid restoration of full blood flow and pressure to ischemic tissue. As described above, the use of thrombolytics and other prior treatments can cause the abrupt removal of an obstruction causing rapid infusion of blood into the ischemic tissue downstream of the occlusion. It is believed that such rapid restoration of full blood flow and pressure, typically at normal physiologic pressures, can result in further damage to the leaky capillary beds and dysfunctional blood-brain barrier which results from the prior ischemic condition.

The present invention allows for a controlled reperfusion of the ischemic tissue where blood can initially be released downstream of the obstruction at relatively low pressures and/or flow rates. That is, it will be desirable to initiate the flow of blood or other oxygenated medium slowly and allow the flow rate and pressure to achieve their target values over time. For example, when actively pumping the oxygenated medium, the pumping rate can be initiated at a very low level, typically less than 30 cc/min, often less than 10 cc/min, and sometimes beginning at essentially no flow and can then be increased in a linear or non-linear manner until reaching the target value. Rates of increase can be from 1 cc/min/min to 360 cc/min/min, usually being from 5 cc/min/min to 120 cc/min/min. Alternatively, the flow of blood or other oxygenated medium can be regulated based on pressure as mentioned above. For example, flow can begin with a pressure in the previously ischemic bed no greater than 10 mmHg, typically from 10 mmHg to 70 mmHg. The pressure can then be gradually increased, typically at a rate in the range from 5–100 mmHg over 2, 8 or even 48 hours. In some instances, it may be desirable to employ blood or other oxygenated medium that has been superoxygenated, i.e., carrying more oxygen per ml than normally oxygenated blood.

While pumping will usually be required to achieve and/or maintain adequate perfusion, in some instances passive perfusion may be sufficient. In particular, perfusion of the smaller arteries within the cerebral vasculature can sometimes be provided using a perfusion conduit having inlet ports or apertures on a proximal portion of the conduit and outlet ports or apertures on a distal portion of the conduit. By then positioning the inlet and outlet ports on the proximal and distal sides of the obstruction, respectively, the natural pressure differential in the vasculature will be sufficient to perfuse blood through the conduit lumen past the obstruction. Usually, the inlet ports on the perfusion conduit will be positioned at a location as close to the proximal side of the occlusion as possible in order to minimize the length of perfusion lumen through which the blood will have to flow. In some instances, however, it may be necessary to position the inlet ports sufficiently proximal to the occlusion so that they lie in a relatively patent arterial lumen to supply the necessary blood flow and pressure. The cross-sectional area of the perfusion lumen will be maintained as large as possible from the point of the inlet ports to the outlet ports. In this way, flow resistance is minimized and flow rate maximized to take full advantage of the natural pressure differential which exists.

While perfusion is maintained through the perfusion conduit, treatment of the blood vessel blockage may be effected in a variety of ways. For example, thrombolytic, anticoagulant and/or anti-restenotic agents, such as tissue plasminogen activator (tPA), streptokinase, urokinase, heparin, or the like, may be administered to the patient locally (usually through the perfusion catheter) or systemically. In a preferred aspect of the present invention, such thrombolytic and/or anticoagulant agents may be administered locally to the arterial blockage, preferably through a lumen in the perfusion catheter itself. Such local administration can be proximal to the thrombus or directly into the thrombus, e.g., through side infusion ports which are positioned within the thrombus while the perfusion port(s) are positioned distal to the thrombus. Optionally, a portion of the blood which is being perfused could be added back to or otherwise combined with thrombolytic and/or anticoagulant agent(s) being administered through the catheter. The addition of blood to certain thrombolytic agents will act to augment the desired thrombolytic activity. The availability of the autologous blood being perfused greatly facilitates such addition. It would also be possible to deliver the agent(s) through the same lumen and distal port(s) as the blood being pumped back through the perfusion lumen so that the agents are delivered distally of the catheter. The latter situation may be used advantageously with neuroprotective agents, vasodilators, antispasmotic drugs, angiogenesis promoters, as well as thrombolytics, anticoagulants, and anti-restenotic agents, and the like. The two approaches, of course, may be combined so that one or more agents, such as thrombolytic agents, are delivered directly into the thrombus while neuroprotective or other agents are delivered distally to the thrombus. Moreover, such delivery routes can also be employed simultaneously with systemic delivery of drugs or other agents to the patient.

Alternatively or additionally, mechanical interventions may be performed while the vasculature is being perfused according to the present invention. For example, a perfusion conduit may have a very low profile and be used as a guide element to introduce an interventional catheter, such as an angioplasty catheter, an atherectomy catheter, a stent-placement catheter, thrombus dissolution device, or the like.

The perfusion of the oxygenated medium may be performed for a relatively short time in order to relieve ischemia (which may be advantageous because of damaged capillaries and/or blood-brain barrier) while other interventional steps are being taken, or may be performed for a much longer time either in anticipation of other interventional steps and/or while other long-term interventions are being performed. In particular, when thrombolytic and/or anticoagulant agents are being used to treat the primary blockage, the perfusion can be continued until the blockage is substantially relieved, typically for at least thirty minutes, often for four to eight hours, or even 2–3 days. In other instances, perfusion can be maintained for much longer periods, e.g., more than one week, more than two weeks, more than a month, or even longer. In some cases, it may even be desirable to maintain perfusion and placement of the perfusion conduit for an extended period of time with the patient having a portable or implantable pump coupled to the conduit. The pump may also have a reservoir for delivery of therapeutic agents and may be implanted or carried on a belt or the like.

The ability of the present invention to provide for gradual or controlled restoration of physiologic blood perfusion pressures and flow rates is a particular advantage when subsequent interventional steps would otherwise result in abrupt restoration of blood flow. As described above, abrupt restoration of blood flow can cause or contribute to reperfusion injuries. By providing for controlled restoration of blood flow prior to such interventional steps, the ischemic tissue can be conditioned to tolerate physiologic blood flow rates and pressures prior to full restoration by dissolution or other removal of the occlusion. Such gradual restoration of blood flow from very low levels to physiologic flow rates can typically be achieved over time periods in the range from one minute, an hour or even up to 48 hours or longer. Perfusion at controlled pressure and/or flow rate may last typically in the range of 30 minutes to 2 hours, more typically 30 minutes to 9 hours. It will be desirable, for example, to initiate perfusion through the perfusion conduits of the present invention at mean arterial pressures downstream of the occlusion which are no greater than 25–50% of normal with typical pressures being 20–40 mmHg. The blood flow rates which correspond to such pressures will depend largely on the nature of the vasculature into which the blood is being perfused and may be less than 200 ml/min, less than 150 ml/min and even less than 100 ml/min.

In addition to delivering oxygen to the ischemic region distal to the primary occlusion, the blood or other oxygenated medium may carry other treatment agents, including thrombolytic agents, anticoagulant agents, tissue preservative agents, and the like. Moreover, in order to further preserve the cerebral tissue distal to the blockage, the oxygenated medium may be cooled to below body temperature, e.g., to a temperature in the range from 2° C. to 36° C., typically from 25° C. to 36° C., in order to cool and preserve the tissue. Cooling may be effected externally as part of the extracorporeal pumping system and/or may be effected using a thermoelectric or Joule-Thomson expansion cooler on the catheter itself.

Patients suffering from ischemia resulting from acute or chronic occlusion in the cerebral vasculature may be treated according to the preferred methods described below. A perfusion conduit is introduced to the patient's vasculature, and a distal port on the conduit is guided through the occlusion in the cerebral vasculature. Blood, optionally oxygenated and/or superoxygenated, is obtained from the patient and perfused back to the patient through the distal port on the conduit past the occlusion at a rate sufficient to relieve the ischemia. The oxygenated blood may be arterial blood which may be returned to the patient without further oxygenation. Alternatively, arterial or venous blood can be oxygenated in suitable apparatus external to the patient and returned to the patient. External oxygenation allows the blood to be "superoxygenated," i.e., oxygenated at higher levels than would normally be available from arterial blood. Usually, the method further comprises delivering a therapeutic agent to the patient while the perfusing step is continued, usually being a thrombolytic agent which is delivered through the conduit directly to the vascular occlusion. The occlusion is usually in either a carotid artery, vertebral artery, proximal subclavian artery, brachiocephalic artery, or an intracerebral artery, and the conduit is usually introduced via the femoral artery in a conventional intravascular approach, typically being positioned over a guidewire which is first used to cross the occlusion. Alternatively, the conduit may be introduced through the axillary or brachial arteries, also in a conventional manner. The conduit may also be advanced through the vasculature and through the occlusion without the aid of a guidewire as will be discussed below.

Apparatus according to the present invention comprises perfusion/infusion catheters which include a catheter body having a proximal end and a distal end. The catheter body has at least a perfusion lumen and may have other lumens. The catheter may be tapered or may have a constant cross-sectional shape. The catheter may be formed as a single, multi-lumen or single-lumen extrusion or the lumens may be formed as separate tubes. When formed as separate tubes, the tubes may be fixed relative to each other or may be provided with appropriate sliding seals to permit them to slide relative to each other. Additional lumens and/or tubes may also be provided for purposes discussed in more detail below. Often, although not always, the catheters will be free from external dilatation balloons or other external structure which could complicate penetration of the distal end of the catheter through an obstruction.

A first embodiment of the catheter is characterized by a large diameter proximal section and a small diameter distal section, where at least two isolated lumens extend from the proximal end of the catheter body through both sections to near the distal end of the catheter body. One of the lumens will extend entirely through the catheter body and usually have side ports over a distal length thereof. The other lumen will usually terminate some distance proximal of the distal tip of the catheter body and will also usually have side ports over a distal length thereof. The proximal section has an outer diameter in the range from 1 mm to 3 mm, usually from 1.5 mm to 2.5 mm, and typically from 1.5 mm to 2 mm, and the distal section has an outer diameter in the range from 0.5 mm to 2 mm, preferably from 0.5 mm to 1.5 mm. The first isolated lumen which extends entirely through the catheter body will usually be tapered, i.e., have a larger diameter over a proximal length thereof than over a distal length thereof. Usually, the first isolated lumen will have an inner diameter in the range from 0.75 mm to 1.25 mm in the proximal section, more usually being from 0.9 mm to 1.1 mm in the proximal section, and an inner diameter in the range from 0.25 mm to 1 mm in the distal section, usually being from 0.3 mm to 0.75 mm in the distal section. The second isolated lumen will usually be disposed annularly about the first isolated lumen and will have an inner diameter in the range from 0.9 mm to 2.9 mm in the proximal section, usually from 1.4 mm to 1.9 mm in the proximal section, and an inner diameter in the range from 0.4 mm to 1.9 mm in the distal section, usually in the range from 0.5 mm to 1.5 mm in the distal section. The second, outer annular lumen will typically terminate from 5 cm to 25 cm from the distal end of the catheter body.

The catheter may also have a larger flow conduit for achieving higher flow rates. For example, the inner diameter of the first lumen may be 1.5–3.0 mm in the proximal section and 1.0–2.0 mm in the distal section. The second lumen has an inner diameter which is preferably 0.25–1.0 mm larger than the outer diameter of the first lumen. The wall thickness of the first lumen is preferably between 0.07–0.20 mm. If the catheter has a straight instead of tapered configuration the inner diameter of the first lumen is preferably 1.5–2.5 mm.

The catheter of the present invention may, of course, have any other suitable tapered shape or may have a constant cross-sectional profile. For example, in another preferred embodiment, the first catheter has the perfusion lumen, and in a specific embodiment no other fluid lumens. Such a catheter has a small, flexible construction which can be passed through tortuous vessels. Other catheters may be advanced over the perfusion catheter to remove or displace the obstruction as discussed below. The catheters may be another fluid perfusion catheter for delivery of thrombolytic agents or may be an obstruction removal catheter which removes the obstruction with mechanical action or with an ultrasound transducer, RF electrode or a laser.

In another aspect of the present invention, the perfusion conduit is advanced through the cerebral vasculature to the obstruction and an obstruction removal catheter is advanced through the perfusion lumen to remove the obstruction. Thus, the perfusion conduit acts as a fluid conduit and/or a guide catheter for reaching distal regions of the cerebral vasculature. The system of the present invention permits the introduction of catheters through the perfusion lumen to regions as distal as the middle cerebral artery M1 and M2 segments, anterior cerebral artery A1 and A2 segments, and the basilar artery or other similarly sized vessels which are typically accessed with guidewires. The obstruction removal catheter may be a balloon, stent, perfusion, RF, ultrasound, laser or mechanical atherectomy catheter for removing the obstruction. As will be discussed below, the catheters of the present invention may also be advanced without the aid of a guidewire.

The present invention is also directed to a system having a balloon catheter and an infusion catheter. The balloon catheter has at least one lumen extending therethrough. The second catheter has a guide tip and fluid infusion openings in a distal region. Both catheters have a proximal region which has a cross-sectional area greater than the distal region. The second catheter is slidably received in the first catheter so that the guide tip and the fluid infusion openings can extend distally from the first catheter.

In another method of the present invention, a method of performing balloon displacement of an obstruction in a patient's vasculature is provided. A balloon catheter is guided over a guidewire to a site in a patient's vasculature. The guidewire is then removed. An infusion catheter is then introduced through the balloon catheter. The infusion catheter is advanced through the balloon catheter so that the tip extends beyond the balloon catheter. An infusate is then delivered through the infusion catheter.

In still another aspect of the present invention, a balloon catheter is provided which is configured to be guided through the perfusion catheter. The balloon catheter has no guidewire lumen and no other structure to track over a guidewire thereby reducing the size of the catheter. The distal end of the balloon catheter preferably has a smooth, rounded tip to penetrate the obstruction if necessary. The balloon catheter may have a tapered shape similar to the perfusion catheter.

The devices of the present invention may be manufactured in any suitable manner. In another aspect of the invention, a preferred method of constructing the devices described above is to position a liner over a mandrel and wind a reinforcing layer over the liner. A jacket is then positioned over the liner and a shrink tube is positioned over the jacket. The entire structure is then heated to fuse the jacket to the liner.

The device preferably has a flexible distal portion to navigate small and tortuous vessels and a stiff proximal portion to provide column strength for advancing the device through the vascular system. The distal portion of the liner is preferably made of expanded PTFE which provides flexibility. The proximal portion of the liner is preferably made of etched PTFE so that the proximal portion has greater stiffness and column strength. An end of the expanded PTFE liner is everted to form a soft, atraumatic distal end.

In a preferred embodiment, the jacket has a number of sections, preferably about five. The jacket preferably has increasing stiffness distally. The flexural modulus of the jacket preferably increases at least 25, more preferably at least 40 times, and most preferably about 55 times from a distal section to a proximal section. Specifically, the jacket flexural modulus increases from 2000 psi at a distal section to 110,000 at a proximal section. The jacket sections also preferably increases in durometer towards the proximal end. The jacket preferably increases at least 13 D, more preferably at least 25 D, over a distance of no more than 10 cm, more preferably no more than 8 cm, for three successive sections. The jacket may also have a fourth section with the first section being at least 25 D less than the fourth section and the first and fourth sections separated by 15 cm or less, more preferably 10 cm or less. The jacket may also have a fifth section with the first section having a durometer which is at least 28 D less than the fifth section. The first section is preferably separated from the fifth section by 20 cm or less and preferably 15 cm or less. The jacket may even have a sixth section with the first section having a durometer which is at least 40 D less than the sixth section. The first and sixth sections are separated by at least 25 cm or even 20 cm.

The reinforcing layer also has a number of sections with the distal section being coil and the proximal sections being braided wire. The braided wire has four sections with decreasing pics toward the proximal end. The first section has a pic which is at least 20 more than the third section. The first section is preferably separated from the first section by no more than 15 cm and preferably no more than 10 cm. The reinforcing layer may also have a fourth section with the first section having a pic which is at least 30 pics more than the fourth section. The first section is separated from the fourth section by no more than 20 cm and more preferably no more than 15 cm.

The catheter of the present invention has a large change in stiffness between the proximal and distal sections. Specifically, the proximal section is at least 20, 40, 60 or even 75 times stiffer than the distal portion of the catheter. The distal portion preferably extends at least 10 or even 15 cm from the distal end while the proximal portion extends to within 40, 35 and most preferably to within 30 cm from the distal end or closer. The high change in stiffness permits the proximal portion to be rigid enough to prevent buckling and kinking while the distal portion is flexible to pass through tortuous vessels. Although the distal portion is relatively flexible, the distal portion still retains a relatively large column strength so that the distal end may be advanced through the vasculature without the aid of a guidewire. A guidewire may, of course, be used at times when needed.

Apparatus according to the present invention further comprise systems including a perfusion/infusion catheter as set forth above in combination with a sheath for percutaneously introducing the perfusion/infusion catheter and a pump for receiving blood from the sheath and delivering blood back to the catheter. Optionally, an infusion device may be provided in the system for infusing a drug to a lumen of the perfusion/infusion catheter. Preferably, the systems will include control apparatus for controlling blood infusion pressures, blood infusion flow rates, pO2, pCO2, pH, temperature, and/or other parameters of the blood/ oxygenated medium being perfused back to the patient. The present invention still further comprises kits, including a perfusion catheter and instructions for use setting forth a method for penetrating the catheter through a blockage in a patient's vasculature and thereafter perfusing an oxygenated medium through the conduit to relieve ischemia. Kits will usually further comprise a container, such as a pouch, tray, box, tube, or the like, which contains the catheter as well as the instructions for use. Optionally, the instructions for use set forth on a separate instructional sheet within the package, but alternatively could be printed in whole or in part on the packaging itself. Optionally, other system components useful for performing the methods of the present invention could be provided within the kit, including guidewires, introductory sheaths, guiding catheters, and the like.

BRIEF DESCRIPTION OF THE DRAWINGS

FIG. 3 is a cross-sectional view taken along line 3—3 of FIG. 2.

FIG. 4 is a cross-sectional view taken along line 4—4 of FIG. 2.

FIG. 5 is a cross-sectional view taken along line 5—5 of FIG. 2.

FIG. 6 is a cross-sectional view taken along line 6—6 of FIG. 2.

FIG. 24 shows another system for treating a cerebral obstruction having first and second tapered catheters.

FIG. 25 is an enlarged view of the distal end of the catheters of FIG. 23.

DESCRIPTION OF THE SPECIFIC EMBODIMENTS

Figure 1A:
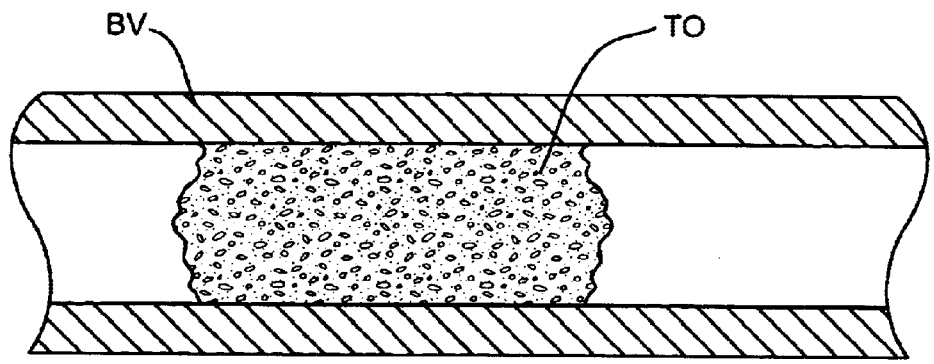
FIGS. 1A–1C illustrate an exemplary protocol for treating a total occlusion in a blood vessel according to the method of the present invention.

The intravascular devices and methods of construction and use are described below. The present invention is described in connection with treating partial or total occlusions but may be used for any other suitable purpose. The general principles for treating partial and total occlusions within a patient's vasculature are described in connection with FIGS. 1A–1C. A blood vessel BV which is usually an artery, more usually a cerebral artery, such as a carotid artery, vertebral artery, or an intracerebral artery, is obstructed by a total occlusion TO. The occlusion may result from thrombosis at a pre-existing atherosclerotic lesion or may result from the shedding of an embolus from an artery which flows distally to the particular vessel in which the occlusion occurs. Usually, the occlusion will occur abruptly and the sudden loss of perfusion through the blood vessel distal to the total occlusion TO will place the patient at great risk of neuron death. As discussed above in the Background section, it is usually necessary to reestablish perfusion within a matter of hours in order to avoid significant tissue damage or death, particularly in the case of strokes. While six hours is often considered a maximum delay, earlier treatment is much more desirable.

The present invention provides a method for very quickly reestablishing perfusion through the total occlusion TO in a controlled manner. Such perfusion is established using a perfusion conduit 10 (FIG. 1C) through which oxygenated blood or an oxygenated synthetic medium, such as a perfluorocarbon oxygen carrier, is actively pumped back through a lumen of the catheter from a source 12. Usually, the conduit will include side perfusion ports 14 near its distal end 16 in order to less traumatically disperse the perfused fluid. Optionally, proximal portions of the conduit 10 (not shown) may have enlarged lumen diameters in order to reduce flow resistance and shear forces to further reduce or prevent hemolysis. It will be appreciated that while the distal portion of the conduit 10 will usually have a relatively low profile to access small diameter blood vessels, the proximal portions can be made significantly larger to improve the hemodynamic flow and handling characteristics and reduce hemolysis.

Figure 1B:
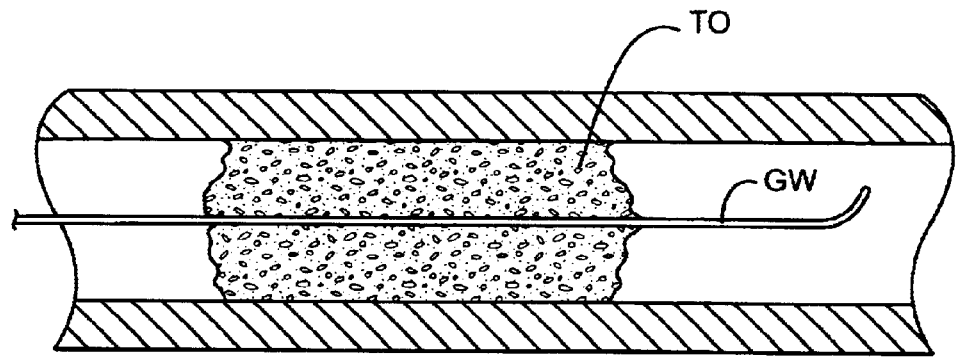
Figure 1C:
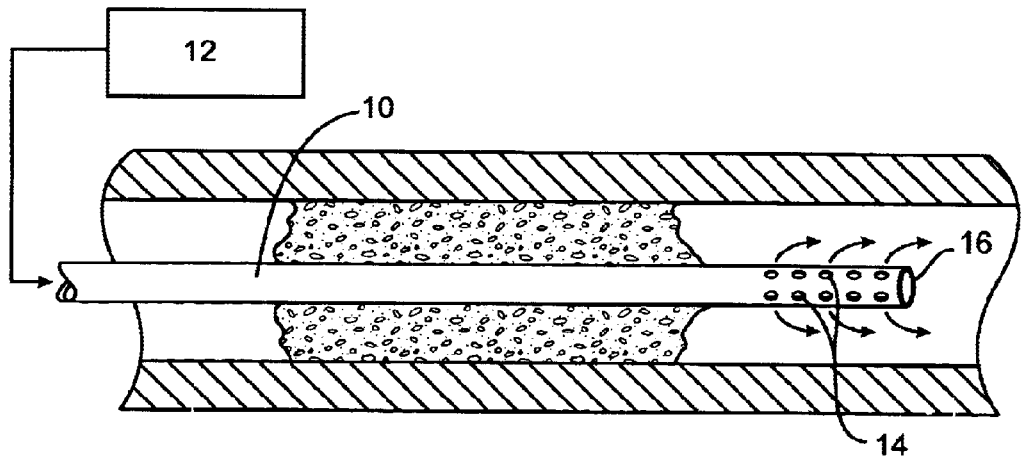

Optionally, the conduit 10 will be introduced over a conventional guidewire GW which may be initially used to cross the total occlusion TO, as shown in FIG. 1B. In other instances, however, the perfusion conduit 10 may be adapted so that it is able to cross the total occlusion TO without the use of a conventional guidewire. In some cases, the perfusion conduit may be in the form of a guidewire, e.g., a tapered guidewire, which is suitable for both guiding through the vasculature to the site of the total or partial occlusion as well as crossing the occlusion.

The perfusion conduit 10 may be introduced from any normal intravascular introduction site, e.g., through the femoral artery using the Seldinger technique. Alternatively, the infusion conduit can be introduced through the axillary and other arteries.

A system 20 suitable for treating occlusions within the cerebral vasculature is illustrated in FIGS. 2–6. The system 20 includes a perfusion conduit in the form of intravascular catheter 22. The catheter 22 comprises a catheter body 24 having a distal end 26 and a proximal end 28. The catheter body 24 comprises a pair of coaxial tubular elements, including an outer tube 30 and an inner tube 32. Proximal hub 34 comprises a first port 36 which is fluidly coupled to an interior lumen of the inner tube 32 and a second port 38 which is fluidly coupled to an annular lumen between the exterior surface of outer tube 32 and the interior of tube 30. Proximal port 40 (typically a hemostasis valve) also communicates with the lumen of the inner tubular member 32 and is suitable for intravascular positioning of the catheter 22 over a guidewire.

The system usually further includes a guiding catheter 50 having dimensions and characteristics suitable for introducing the catheter 22 to the desired intravascular target site. Although illustrated as having a straight configuration, the guiding catheter 50 will often have a preformed, curved tip selected specifically to reach the intravascular target site, and the guiding catheter could further be reinforced (e.g., braided), have a variable stiffness over its length, have a variable diameter, or the like. The system 20 will usually still further comprise a sheath 60 which is used to percutaneously access the vasculature at the introductory site, e.g., in the femoral artery. The sheath 60 has a proximal hub 61 including at least one side arm 62. The hub 61 receives the catheter 22 therethrough and will include a mechanism for maintaining hemostasis about the catheter. The side arm 62 permits withdrawal of blood for oxygenation and return to the patient according to the present invention. Other side arm(s) may be provided for removal of blood (optionally combined with drugs being delivered back to the patient), for infusing agents through the sheath 60, or for other purposes. Entry of blood into the lumen of the sheath is optionally facilitated by side ports 64 formed over at least a distal portion of the sheath. The catheter body 24 is tapered in the distal direction, i.e., the diameter is larger near the proximal end 28 than at the distal end 26. As illustrated in FIGS. 2–6, the outer tube 30 has a large diameter proximal section (observed in FIG. 3) and a smaller diameter distal section (observed in FIGS. 4 and 5). Similarly, the inner tube 32 has a large diameter proximal section (shown in FIG. 3) and a smaller diameter distal section (shown in FIGS. 4–6). The particular outer diameters and inner lumen diameters of both the outer tube 30 and inner tube 32 are within the ranges set forth above. Since the distal terminii of the outer tube 30 and inner tube 32 are staggered, the catheter body 24 is tapered in three stages, with a first diameter reduction occurring at location 33 (FIG. 2) where the diameter of the outer tubular member 30 is reduced from the diameter shown in FIG. 3 to the diameter shown in FIG. 4. The second diameter reduction occurs at location 35 where the outer tubular member 30 terminates, leaving the outer surface of the inner tubular member 32 to define the catheter body.

Such tapered configurations are preferred since they maximize the cross-sectional area of the flow lumens over the length of the catheter to reduce flow resistance for both the blood (or other oxygenated medium) and the drug to be delivered. As can be seen in FIG. 3, lumen 70 of the inner tubular member 32 which carries the blood is maximized until the diameter is reduced near the distal end of the catheter, as shown in FIG. 4. Similarly, the annular lumen 72 which carries the drug is maximized over the proximal portion before it is reduced after the transition at location 33. Maintaining the larger diameters and lumen areas is desirable in order to decrease flow resistance and shear forces to reduce or eliminate hemolysis as the blood is introduced through the entire catheter length. Similarly, a reduction in flow resistance to the drug being introduced facilitates drug delivery during the procedure.

Figure 2:
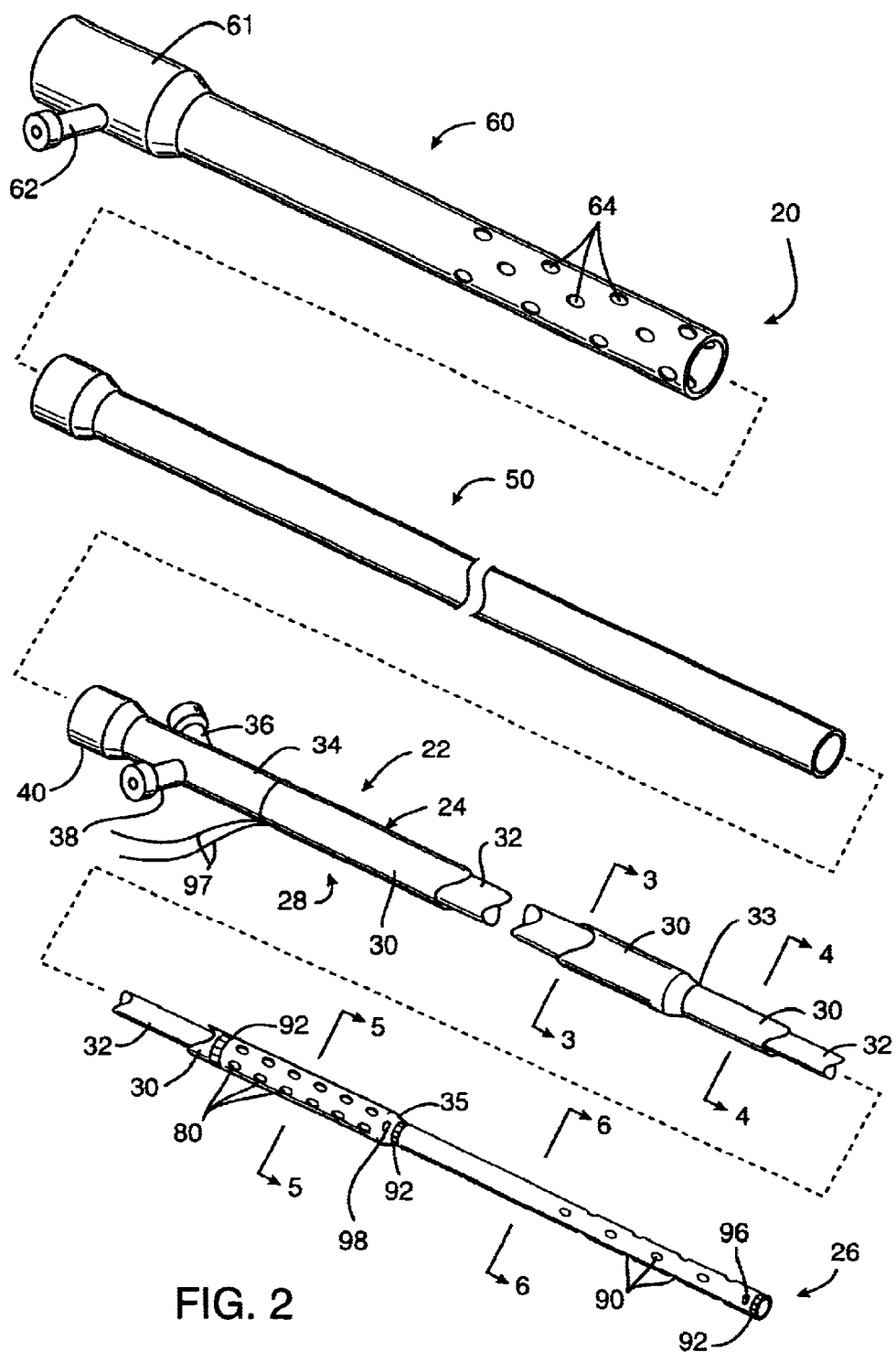
FIG. 2 illustrates an exemplary system for treating a total occlusion within a patient's cerebral vasculature according to the present invention.

Side wall penetrations 80 are provided in a distal portion 26 of the outer tubular member 30, as best seen in FIGS. 2 and 5. The penetrations 80 will be useful for delivering a therapeutic agent through port 38 in order to treat the primary occlusion, as described in more detail hereinafter.

Similarly, ports 90 may be formed over at least a distal portion of the inner tubular member 32 which extends beyond the distal end of the outer tubular member 30. The penetrations 90 will be available to release blood or other oxygenated medium that is being perfused back to the patient through port 36 and the continuous lumen of the tube 32. Note that while the lumen 70 of tube 32 will be available for introduction of the catheter 22 over a guidewire, the guidewire may be at least partially withdrawn from the lumen 70 in order to further decrease blood flow resistance as it is perfused back to the patient.

Optionally, the catheter 22 may comprise at least one pressure sensing element 96 disposed at a location near where the blood or other oxygenated medium is returned to the blood vessel. Preferably, the pressure sensing element 96 may be a piezoelectric or other solid state pressure sensing device and will be connected through the hub 34 by a pair of wires 97 which may be connected to conventional electronic devices for measuring pressure. Thus, pressure may be measured and used for controlling rate and/or pressure of blood or other oxygenated medium pumped back to the patient using conventional analog or digital control circuitry. A pressure control point will be selected, usually within the ranges set forth above, and the rate or pressure of oxygenated medium being pumped back through the catheter 22 will be controlled to maintain the control point. Conventional control algorithms, such as proportional, derivative, integral, and combinations thereof, may be employed for maintaining the desired control point.

In some instances, it will be desirable to provide at least a second pressure sensing element 98 which will be located proximal to the obstruction when the catheter is in use. For example, the pressure sensing element 98 may be near the location 35 where the outer tubular member 30 terminates. The sensor 98 will permit monitoring of the pressure in the vasculature proximal of the occlusion, which pressure will usually approximate that of the vasculature in the region of the occlusion prior to an acute occlusion event. This pressure, in turn, may be utilized as a target pressure for the blood or other oxygenated medium which is being perfused distal to the occlusion. That is, it may be desirable to treat the measured "background" pressure as a maximum desirable pressure for perfusion in order to prevent injury to the vasculature distal to the occlusion.

Figure 7:
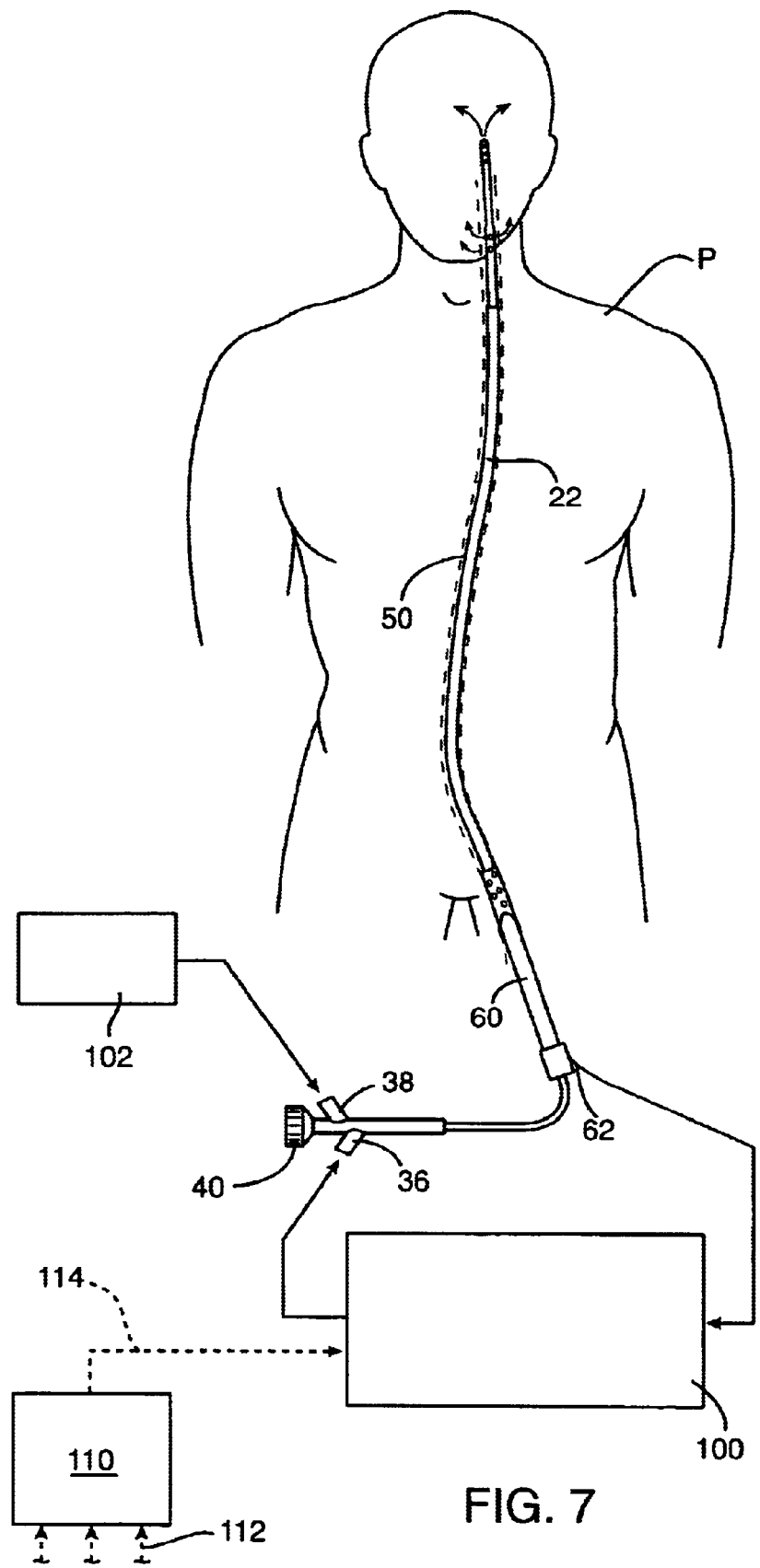
FIG. 7 illustrates a protocol using the system of FIG. 2 for treating a cerebral occlusion according to the present invention.
Figure 8:
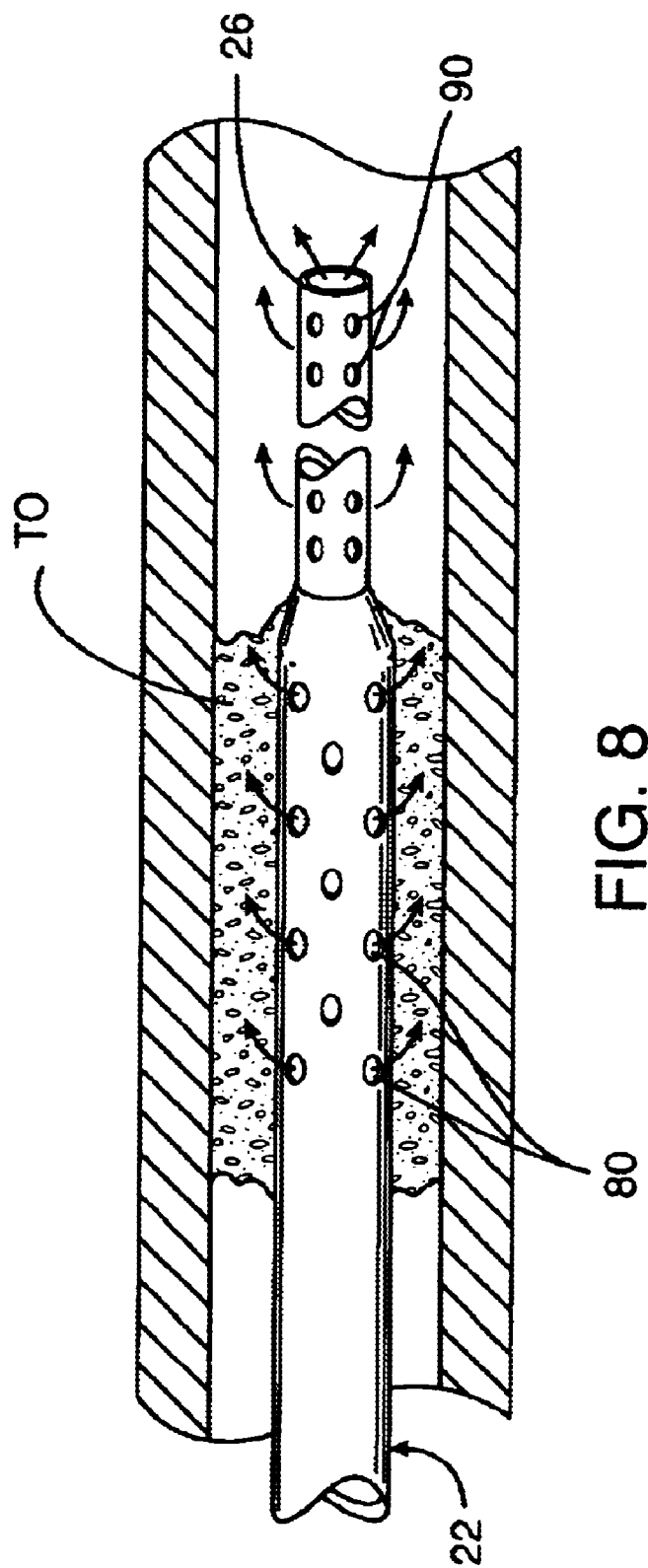
FIG. 8 is a detailed view of the catheter used for treating the occlusion in the protocol of FIG. 7.

Referring now to FIG. 7, use of the system 20 for treating the cerebral vasculature of a patient P will be described. Access to the target cerebral artery is established using the sheath 60 in a conventional manner. The guiding catheter 50 is then introduced through the sheath 60 and establishes a protected access lumen to a location within the cerebral vasculature. The catheter 22 is then introduced through the guiding catheter to the target site within the cerebral vasculature, typically over a guidewire (not illustrated). Conveniently, the catheters will be partly radiopaque and/or radiopaque markers 92 (FIG. 2) will be provided at the distal tip of the catheter as well as on either side of the drug ports 80 so that the catheter 22 may be properly positioned under fluoroscopic guidance relative to the obstruction being treated. After the tip 26 of the catheter 22 is penetrated through the occlusion TO (FIG. 8) the penetrations 80 are preferably located within the occlusive material in order to deliver the thrombolytic or other agent to the material. The distal portion of the catheter, including ports 90, in contrast, are located beyond the occlusive material in order to provide the desired blood perfusion. Blood flow is immediately established using an external pump 100 which receives blood from the port 62 of access sheath 60 and returns the oxygenated blood to the catheter 22 through port 36. Any suitable therapeutic agent, such as a thrombolytic agent, may be introduced through port 38 from a source 102. Any other suitable drugs may also be delivered from the source 102 and through the port 38. Optionally, the blood may be cooled before, during, or after it has passed through the pump unit 100. Still further optionally, the blood may be oxygenated or superoxygenated using an oxygen-saturated bubble chamber or conventional cardiopulmonary bypass oxygenators ORS. In some instances, it may be desirable to combine the thrombolytic agent with a portion of the recirculating blood before infusing the thrombolytic agent/blood back through the port 38.

Optionally, the pump unit 100 may be controlled by an analog or digital control unit 110 (FIG. 7). The control unit 110 will receive various input control parameters 112, typically including at least oxygenated medium flow rate and pressure. Other control parameters, such as pO2, pCO2, pH, temperature, and the like, may also be input into the control unit 110. In turn, the control unit will provide a control output 114, typically at least to the pump unit 100 to control output flow and pressure, as described above. If control of other parameters is desirable, other capabilities may be added, such as the ability to control the degree of oxygenation in the medium supplied by source 102, the ability to add pH modifiers, such as buffers, bicarbonate, and the like, to the oxygenated medium, the ability to control a heat exchanger located in the blood flow circuit, and the like. The source 102 may provide any of the various drugs or therapeutic agents described herein for delivery through the ports.

Figure 9:
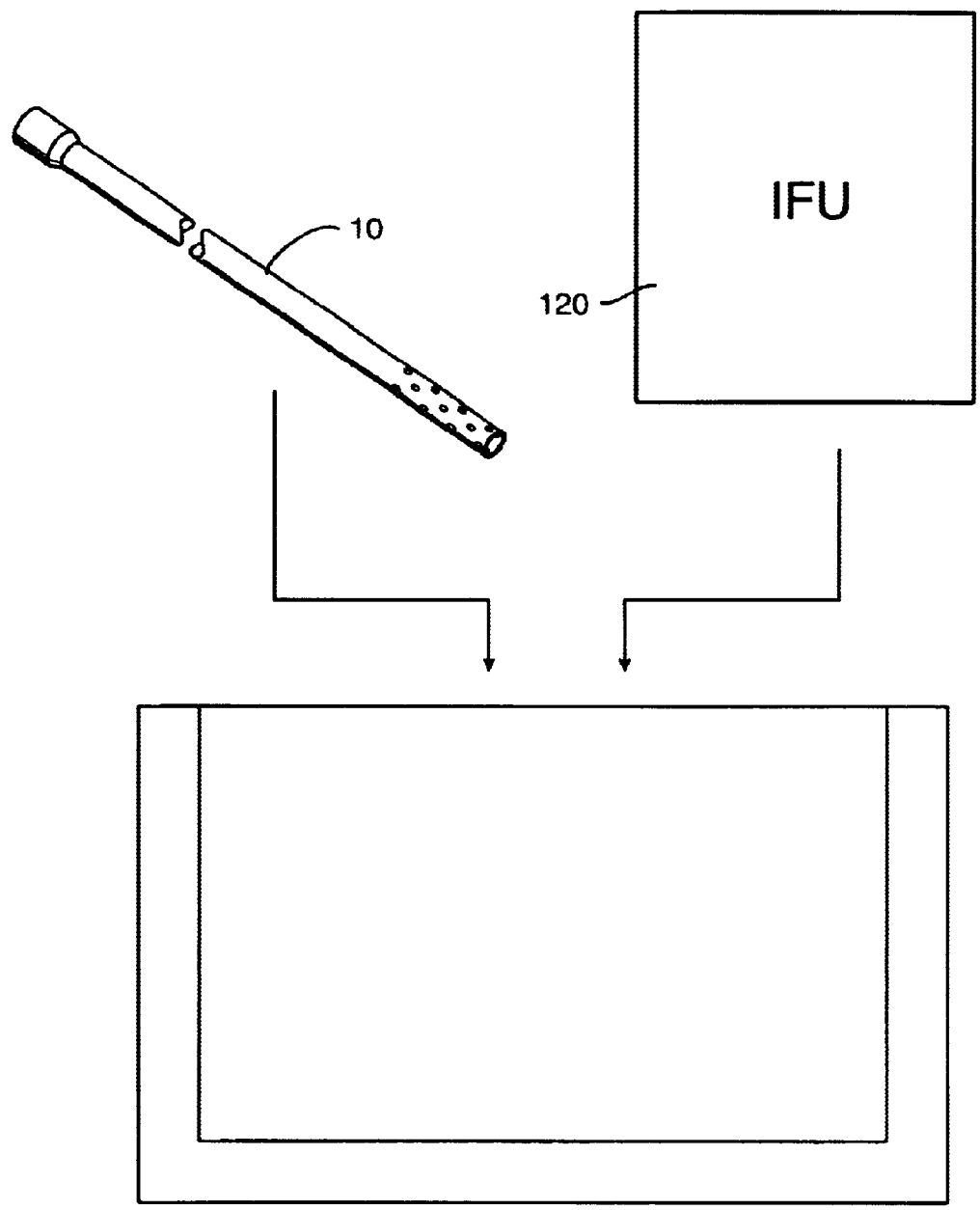
FIG. 9 illustrates a kit including components according to the present invention.

Kits according to the present invention are illustrated in FIG. 9. The kit will include a perfusion conduit, such as perfusion conduit 10, as well as instructions for use 120. The catheter and instructions for use will usually be combined within a suitable container, such as a pouch, tray, box, tube, or the like. The catheter and possibly other components of the system (such as guide catheters, sheaths, thrombolytic or other therapeutic agents, disposable cartridges for pump/oxygenation systems, or the like) will optionally be included and/or sterilized within the packaging. The instructions for use may be on a separate sheet of paper or may be printed in whole or in part on the packaging materials. The instructions will set forth a method of using the devices in any manner described herein. Furthermore, the kit may include any grouping of instruments described herein without departing from the scope of the invention.

Figure 10:
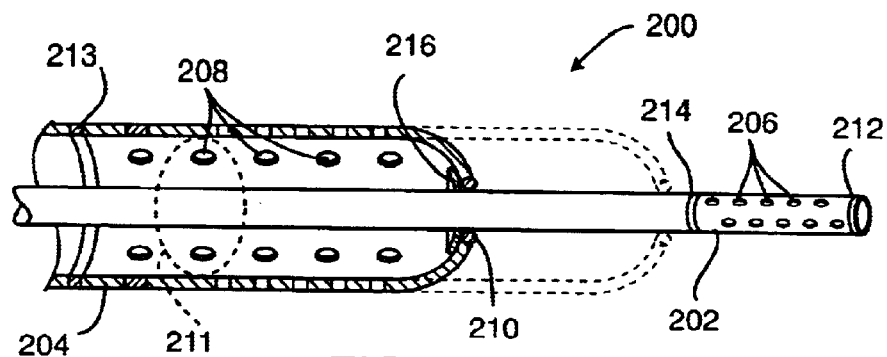
FIG. 10 illustrates an alternative embodiment of a perfusion conduit constructed in accordance with the principles of the present invention.

Referring now to FIG. 10, a perfusion conduit 200 includes an inner tube 202 and outer tube 204. The inner tube has perfusion ports 206 formed in its side wall over a portion of the distal end, and the outer tube 204 has perfusion ports 208 formed over a portion of its distal end. The perfusion conduit 200 differs from catheter 22 primarily in that the inner tubular member 202 is able to slide axially relative to the outer tubular member 204. A sliding seal 210, typically an O-ring or similar passive seal, is provided to maintain pressure within the lumen of outer tubular member 204 so that thrombolytic and other drugs can be delivered without excessive loss through the distal tip. Some loss of the agent, however, will usually be acceptable so that the seal need not be completely tight. If a more positive seal is desired, an inflatable balloon 211 (shown in broken line) may be provided in addition to or in place of the sliding seal 210. Use of the balloon 211 is advantageous in that it permits higher infusion pressures without leakage from the distal end of the outer tube 204, but disadvantageous in that it limits the range of axial placement of the outer tube 204 relative to the inner tube 202. Use of the inner tube 202 for perfusing blood or other oxygenated medium therethrough will generally be as described with the prior embodiments. Radiopaque markers 212 and 214 on the inner tube 202 will be positioned distally of the occlusion to assure that the perfusion ports 206 will release the delivered blood with minimal resistance. Radiopaque markers 216 and 218 on outer tube 208, in contrast, will be positioned so that the infusion ports 208 lie generally within the occluded region. Optionally, the balloon 212 will be inflated to both lock the inner and outer tubes relative to each other and to provide a positive seal at the distal end of the outer tube, and the thrombolytic or other therapeutic agent will then be delivered through the lumen of the outer tube into the occlusive material, such as thrombus.

Figure 11:
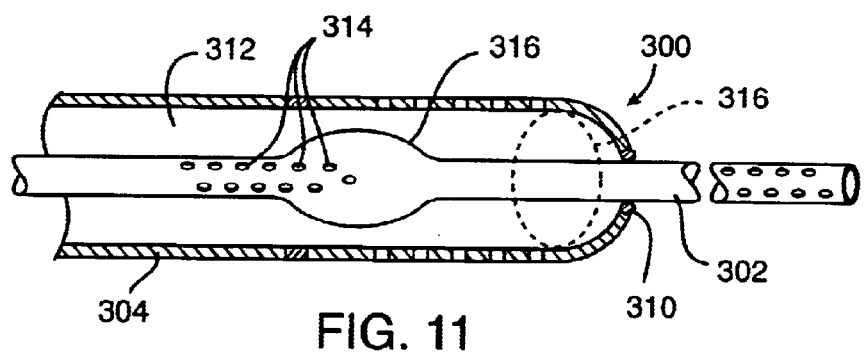
FIG. 11 illustrates yet a further embodiment of a perfusion conduit constructed in accordance with the principles of the present invention.

Referring now to FIG. 11, a perfusion conduit 300 also includes an inner tube 302 and an outer tube 304. The inner and outer tubes are slideable relative to each other, and a sliding seal 310 is provided at the distal end of the outer tube 304. The perfusion conduit 300, in contrast to prior embodiments, is not intended to deliver a therapeutic agent. Instead, it is intended only to perfuse blood or other oxygenated medium therethrough. The lumen 312 within the outer tube 304 is intended for passing the blood or other oxygenated medium to near the distal end of the conduit 300. The inner tube 302 then receives the blood or other oxygenated medium through ports 314 which permit the medium to flow from lumen 312 into the interior lumen of the tube 302. An enlarged portion 316 of the tube 302 is provided in order to prevent axial advancement of the tube so that the ports 314 cannot extend outside of the outer tube 304. Alternatively or additionally, an inflatable balloon 316 may be provided in order to both prevent excess axial advancement of the inner tube 302 and provide a more positive seal. Usually, since the blood will be perfused at lower pressures than might be used for drug delivery, use of the balloon 316 for isolation will often not be necessary. The perfusion conduit 300 can thus provided reduced flow resistance for the blood or other oxygenated medium being returned to the patient through the conduit. Additionally, the ability to slide the outer tube 304 relative to the inner tube 302 helps the tubes be properly positioned relative to each other depending on the circumstances of the patient being treated.

Figure 12:
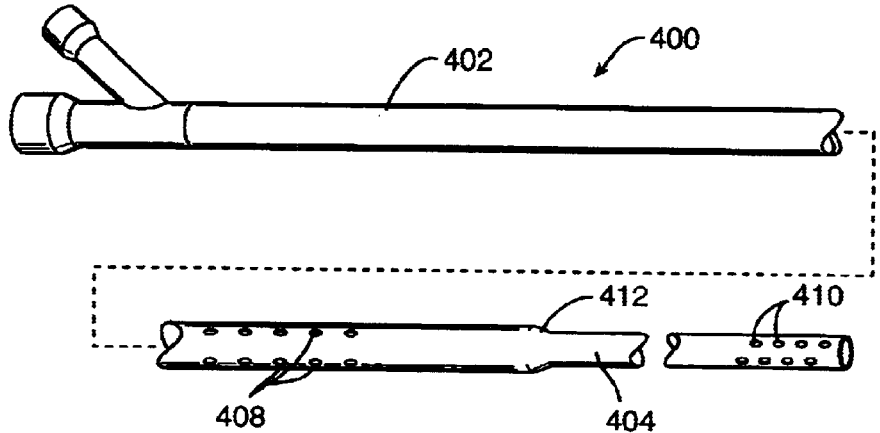
FIG. 12 illustrates yet another exemplary embodiment of a perfusion conduit constructed in accordance with the principles of the present invention.

Referring now to FIG. 12, a perfusion conduit 400 intended for passive perfusion, i.e., without active pumping, is illustrated. The catheter 400 usually comprises a single extrusion having a proximal section 402 with an enlarged diameter and a distal section 404 with a reduced diameter. The proximal and distal diameters will generally be in the ranges set forth above. Blood inlet ports 408 are provided on the catheter near its proximal end while blood outflow ports 410 are provided near the distal end. The relative positions of the inflow ports 408 and outflow ports 410 allow the perfusion conduit 400 to be introduced to a patient so that the inflow ports are proximal to the occlusion while the outflow ports 410 are distal to the occlusion. The inflow ports 408 are usually relatively near to the distal end of the proximal section 402 having the enlarged diameter in order to decrease the overall flow resistance between the inflow ports 408 and outflow ports 410. Generally, however, the inflow ports 408 will be positioned so that they will lie proximally of the occlusion so that the occluding material does not block blood flow into the inflow ports. In some instances, they will be spaced proximally of the transition 412 from large diameter to small diameter by a distance in the range from 1 cm to 15 cm, usually from 2 cm to 10 cm, to assure proper placement in the vasculature. The inflow ports 408 are thus able to receive blood and pass the blood distally through the large diameter section with minimum pressure drop. A pressure drop through the narrow diameter section 404 will be greater, in many instances the total pressure drop of the conduit 400 will be sufficiently low so that adequate blood perfusion can be maintained to relieve patient ischemia. Optionally, the conduit 400 could have a slideable structure, as shown in conduit 300 of FIG. 11, but such structure will increase the flow resistance and will not be preferred in all instances. The conduit 400 preferably has a ID of 0.5 mm to 1.8 mm, more preferably 0.75 to 1.5 mm, between the inflow and outflow ports.

Figure 13:
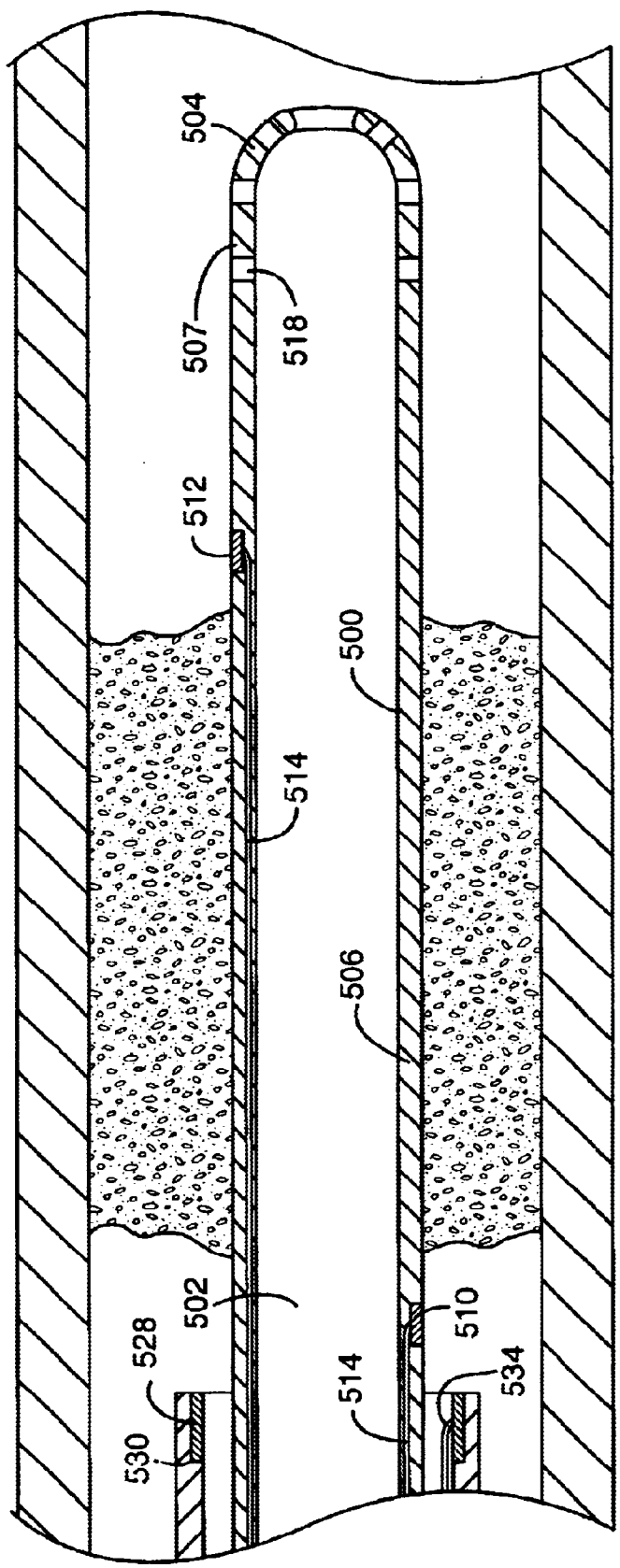
FIG. 13 illustrates another perfusion catheter with a second catheter advanced over the perfusion catheter.
Figure 14:
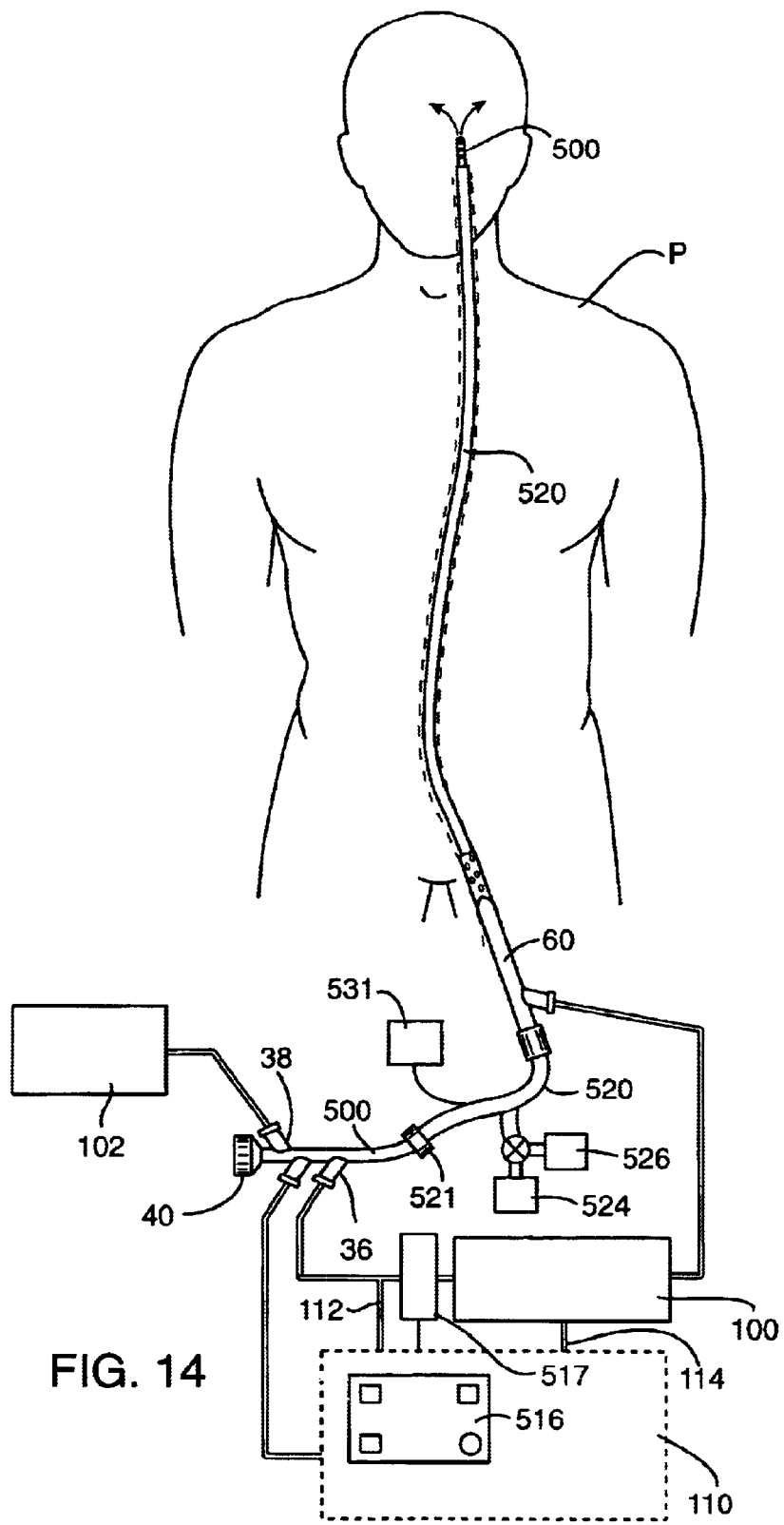
FIG. 14 illustrates a perfusion used in connection with the catheters of FIG. 13.

Referring to FIGS. 13 and 14, another catheter 500 is shown which has a perfusion conduit 502. The catheter 500 has a rounded, atraumatic distal end 504 which is preferably guided through the vasculature over a guidewire which is advanced ahead of the catheter 500. The perfusion conduit 502 may have any of the shapes and sizes discussed herein and preferably has a cross-sectional size of 0.77 to 7.1 mm2, more preferably 1.7 to 2.9 mm2 along a distal portion 506 of the catheter 500. In order to maintain adequate flow rates at acceptable pressures, the cross-sectional size is preferably at least 1.7, more preferably at least 3.0 and most preferably at least 4.2 mm2 along the distal portion 506. The distal portion 506 extends for a length of at least 5, 10,15, 20 or 25 cm from distal end 507 or from the most proximal outlet 518.

The catheter 500 and conduit 502 are sized large enough to provide sufficient blood flow rates while blood pressure is within allowable limits to prevent hemolysis. Specifically, the conduit 502 is sized so that the pressure of oxygenated blood in the catheter is 0–400 mmHg, more preferably 20–350 mmHg, at blood flow rates of at least 30, 80, 120 or 160 ml/min. Furthermore, the overall length of the catheter 500 is preferably at least 120, 150 or 175 cm depending upon the access site and size of the patient.

The overall maximum outer dimension of the catheter 500 shaft along the distal portion 506 is preferably no more than 1.6 mm, 2.3 mm, or 3.2 mm. The various diameters and dimensions given throughout the application are equally applicable to any other suitable embodiments described herein. For example, all catheter dimensions discussed above are suitable dimensions for catheter 500 and all dimensions for catheter 500 are applicable to other catheters described herein. Although catheter 500 may include additional open lumens, such as balloon inflation, vent or pressure lumens, the catheter 500 preferably includes only the perfusion conduit 502 to minimize the overall size. The catheter 500 may also be a passive inflation catheter such as the passive inflation catheter 400 of FIG. 12.

The catheter 500 may include proximal and distal pressure sensors 510, 512 for measuring pressure on both sides of the obstruction. In a preferred embodiment, the catheter 500 has only one pressure sensor 512 and only the perfusion conduit 502. Wires 514 extending through or along shaft are coupled to a pressure monitor 516 which in turn is integral with or coupled to the control unit 110 for controlling the pump 100 in any manner described herein. The distal pressure sensor 512 is preferably positioned a distance A which is at least 0.5 cm more preferably at least 1 cm, from the most proximal outlet 518 so that pressure measurement is not distorted by flow forces from the fluid perfused through the outlets 518. A heater and/or cooler 517 is also provided for heating or cooling the oxygenated medium. The control unit 110 also receives input control parameters 112 with the parameters measured with suitable sensors along the fluid line.

The pressure is preferably maintained below normal arterial pressure for a period of time to protect the previously ischemic bed from reperfusion injury. The inventor believes that prematurely exposing the ischemic bed to normal arterial pressure may cause reperfusion injury and that maintaining low pressure for a period of time can minimize or eliminate reperfusion injury. Low pressure in the previously ischemic bed can be maintained by pressure feedback control of the pump 100 as mentioned above. Alternatively, low pressure can be maintained without direct measurement and feedback by simply selecting low perfusion flow rates.

A second catheter 520 is slidably coupled to the catheter 500 and is advanced into the vascular system with the catheter 500 guiding the second catheter 520 to the obstruction. The catheter 500 passes through a hemostasis valve 521 in the second catheter 520. The second catheter 520 passes over the catheter 500 but may also have an interlocking relationship with the catheter 500. The second catheter 520 may also be completely independent from the catheter 500 since advancing the second catheter 520 quickly may not be necessary with catheter 500 perfusing and protecting the previously ischemic vascular bed.

The second catheter 520 has a lumen 522 defined by the annular space between the catheters 500, 520. The lumen 522 may be used to deliver liquids, including any of the therapeutic agents described herein such as a thrombolytic agent, from a liquid source 524. The second catheter 520 may also be coupled to a vacuum source 526 to vent blood, therapeutic byproducts and emboli through lumen 522.

The second catheter 520 may also include an obstruction removal device 528 for removing the obstruction. The obstruction removal device 528 may simply be the distal tip of the catheter 520 which is used to mechanically remove the obstruction. The obstruction removal device 528 may also be any suitable non-mechanical device such as an ultrasound transducer, an RF electrode, or a laser. FIG. 13 shows the obstruction removal device 528 as an ultrasound transducer coupled to a power source 531 (FIG. 14) with wires 534. The wires 534 may float within lumen 522 or may be embedded in the wall of the catheter 520. If the obstruction removal device is an RF electrode, a suitable second electrode (not shown) is placed in contact with the patient's body for monopolar RF or on either catheter 500, 520 for bipolar RF. An electrically conductive fluid, such as saline, may be passed through the lumen 522 from the liquid source 524 during activation of the RF electrode for enhanced conduction. Thus, the second catheter 520 is used to remove the obstruction by mechanical disruption, delivery of obstruction removing liquids through the lumen 522 or use of any of the other suitable devices mentioned above.

Figure 15:
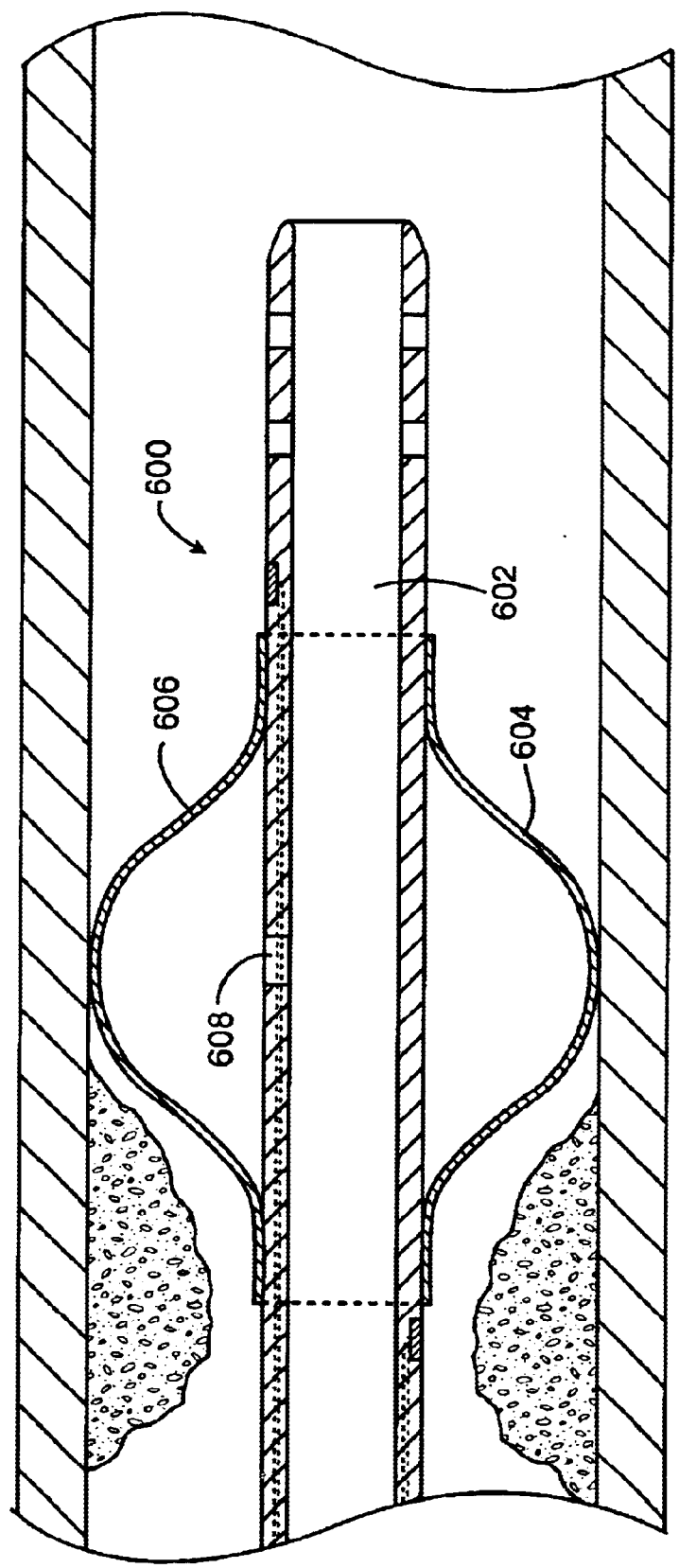
FIG. 15 illustrates another perfusion catheter having a balloon inflated by fluid infused through the fluid lumen.

Referring to FIG. 15, another perfusion catheter 600 is shown which has a perfusion conduit 602. The catheter 600 also has an expandable member 604 which is preferably an inflatable balloon 606 but may also be a mechanically actuated device. The expandable member 604 prevents the previously ischemic bed from being exposed to full arterial pressure if the obstruction is cleared prematurely before the perfusion therapy is completed. The balloon 606 may also be used to prevent parts of the obstruction or other emboli from flowing downstream before therapeutic agents or other obstruction removing methods are used to dissolve, destroy, displace or otherwise remove the obstruction.

Figure 16:
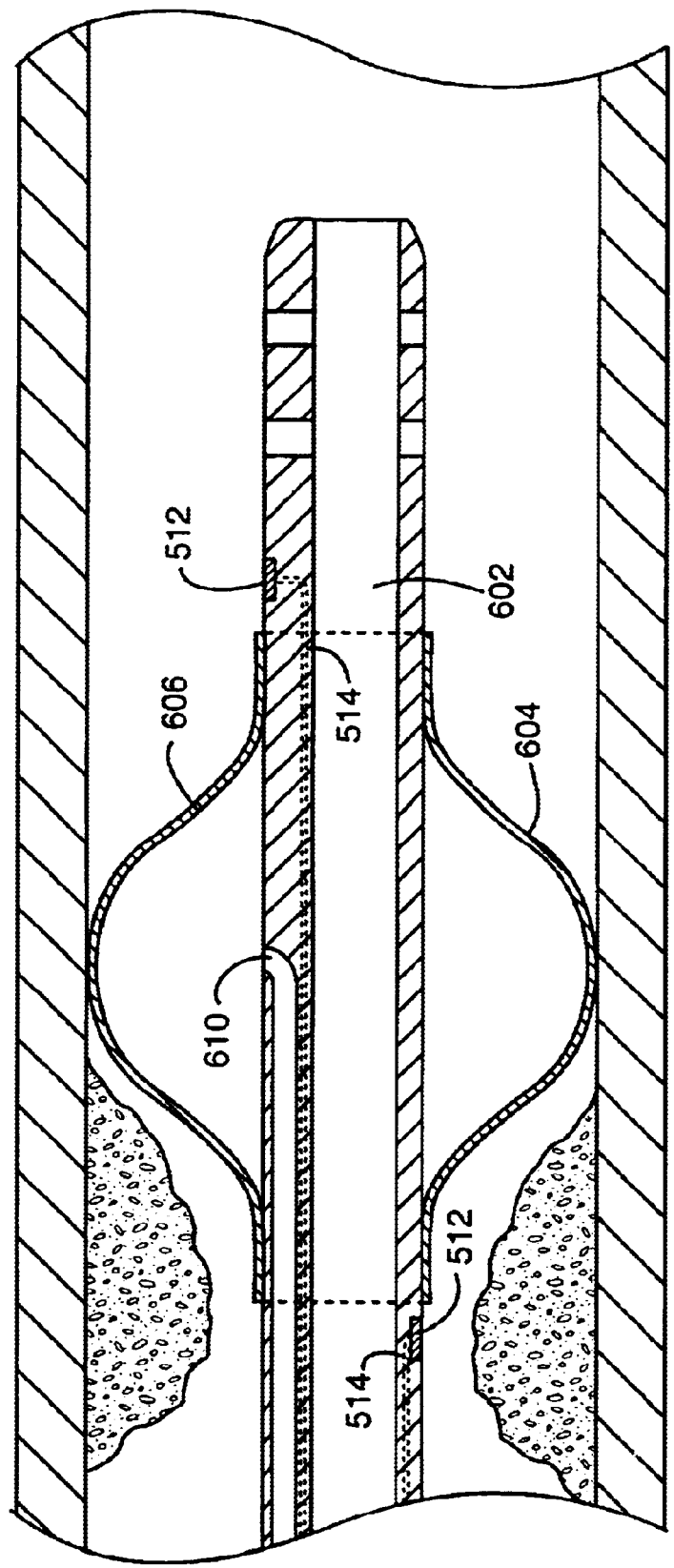
FIG. 16 illustrates a still another perfusion catheter having a balloon with an inflation lumen.

The balloon 606 has an inflation hole 608 leading to the perfusion conduit 602 so that perfusion of fluid through the conduit 602 inflates the balloon 606. An advantage of using the perfusion conduit 602 to inflate the balloon 606 is that a separate inflation lumen is not required which minimizes the size of the catheter 600. Referring to FIG. 16, the perfusion catheter 600 may also include a separate inflation lumen 610 for inflating the balloon 606 so that the balloon 606 may be selectively inflated independent of perfusion. The balloon 606 may also be used for flow-directed placement of the catheter 600.

Figure 17:
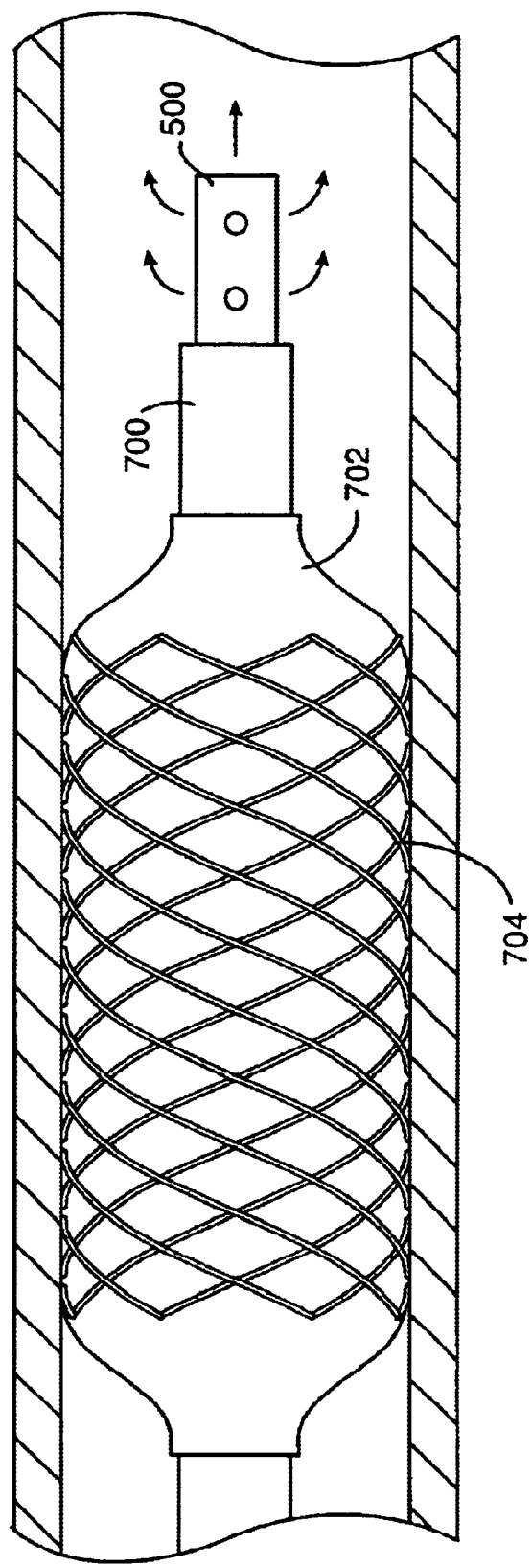
FIG. 17 illustrates a perfusion catheter with a stent delivery catheter advanced over the perfusion catheter.
Figure 18:
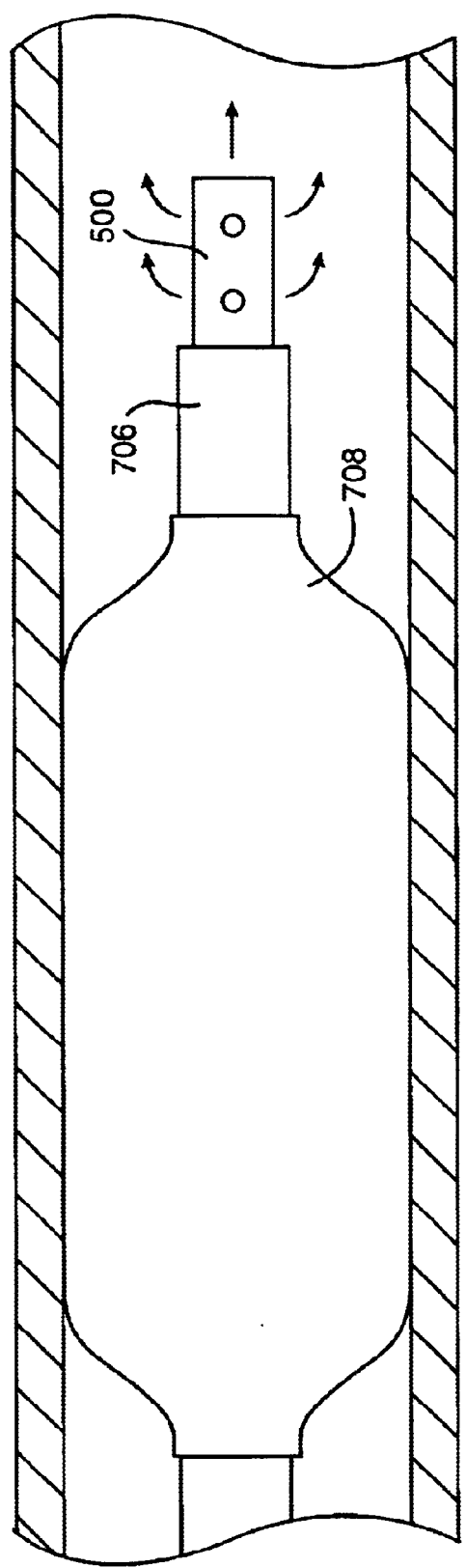
FIG. 18 illustrates a perfusion catheter with a balloon catheter advanced over the perfusion catheter.

Referring to FIG. 17, a stent delivery catheter 700 is passed over the perfusion catheter 500, which may be any of the perfusion catheters described herein, and a balloon 702 is used to expand a stent 704 and open the artery. Referring to FIG. 18, a balloon catheter 706 having a balloon 708 is advanced over the perfusion catheter 500. The balloon 708 is expanded in the obstruction to displace the obstruction and open the artery. An advantage of the present system is that the perfusion catheter 500 perfuses and protects of the previously ischemic bed while the stent 704 or balloon 708 is positioned and deployed.

Figure 19:
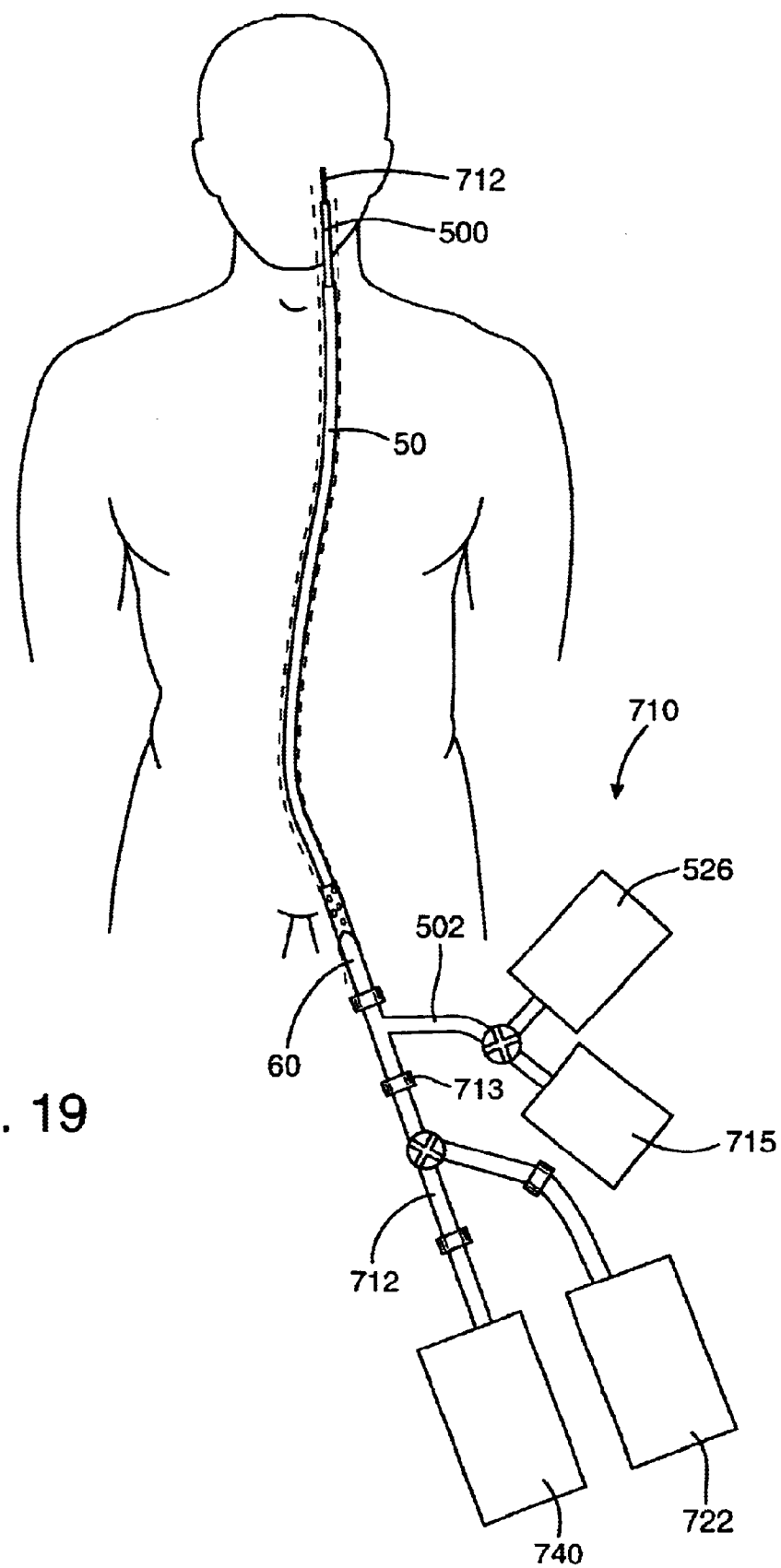
FIG. 19 shows another system for treating a cerebral obstruction.

Referring to FIG. 19, another system 710 for treating the cerebral vasculature is shown. The system 710 includes the catheter 500 which may be any of the catheters 10, 400, 600 described above or any other suitable alternative. A catheter 712 passes through the catheter 500 and is used to remove or displace the obstruction in the cerebral vasculature. As will be described in specific embodiments below, the catheter 712 may be a balloon catheter 714 (FIGS. 20 and 21), a stent catheter 716 (FIG. 22) or a perfusion catheter 718 (FIG. 23). The catheter 712 may, of course, use any other suitable method for removing the obstruction including a laser, microwave, ultrasound, RF or a mechanical device.

The system 710, and in particular the catheter 500, may also be used in any manner described above. For example, the catheter 500 may be used to infuse oxygenated medium to treat an ischemic region prior to introduction of catheter 712. After infusion of the oxygenated medium for a period of time, the catheter 712 is used as described below. The catheter 500 preferably has the dimensions and characteristics of any suitable catheter described herein. In particular, the lumen 502 preferably has the necessary dimensions to provide for adequate infusion while being small enough to provide a flexible catheter which can pass into distal regions of the cerebral vasculature. The distal portion is preferably at least 5, 10 15 or 20 cm in length. The lumen along the distal portion has a cross-sectional area of 0.45 to 2.3, more preferably 0.62 to 1.8, and most preferably 0.62 to 1.7 mm2. When the cross-sectional shape of the lumen is circular, the diameter of the lumen 502 is preferably 0.76–1.52 mm, more preferably 0.89–1.40 mm and most preferably 0.89–1.27 mm along the distal portion. The maximum cross-sectional dimension along the distal portion (which is simply the outer diameter for a circular cross-section) is preferably no more than 0.41 mm, 0.31 mm or 0.20 mm larger than the diameter of the lumen 502. Thus, the maximum cross-sectional dimension is preferably no more than 1.2, 1.1 or 1.0 mm when the diameter of the lumen 502 is 0.76 mm.

The catheter 500 also preferably has a proximal portion which extends for a length of at least 75 or 100 cm. The lumen 502 has a cross-sectional area of 2.0–7.6, more preferably 2.8–5.6 mm2, and most preferably about 3.2–5.1 mm2 along the proximal portion. When the lumen 502 has a circular cross-sectional shape, the lumen 502 has a diameter of 1.52–2.92 mm, more preferably 01.09–2.67 mm, and most preferably 1.89–2.54 mm. The maximum cross-sectional dimension along the proximal portion is preferably no more than 0.41, 0.31 or 0.20 mm larger than the diameter of the lumen 502. The catheter 500 may also have an intermediate section which has a length of 20–40 and preferably about 30 cm. The intermediate section has a cross-sectional size between the size along the proximal and distal sections. In a preferred embodiment, the intermediate section has a constant taper between the proximal and distal portions.

The catheter 500 has a hemostasis valve 713 which receives the catheter 712. The introducer sheath 60 may also be used for introducing the catheter and for withdrawing and directing blood and other fluids from a fluid system 715 which is the system of FIGS. 7 or 14 described above.

An advantage of the catheter 500 is that the catheter 500 can be used to guide the balloon catheter 714, or any other catheter, to distal portions of the cerebral vasculature. Specifically, the catheter 500 is flexible enough to reach the middle cerebral artery M1 and M2 segments, anterior cerebral artery A1 and A2 segments, and basilar artery and preferably to distal regions which are accessible depending upon the size of the patient's vasculature. These regions are typically accessed by advancing the catheter over a guidewire rather than through another catheter. An advantage of using the catheter 500 rather than a traditional guidewire is that the catheter 500 protects the vasculature as the catheter 500 is advanced. Another advantage is that the catheter 500 may be used to infuse fluids, such as the oxygenated medium and therapeutic agents prior to, during and after introduction of the obstruction removal catheter 712.

Referring to FIGS. 19 and. 20, the balloon catheter 714 has a balloon 718 which displaces the obstruction. An inflation lumen 720 is coupled to a source of inflation fluid 722 (FIG. 19) for inflating the balloon 718. The catheter 714 may have more lumens, however, the catheter 714 has only the inflation lumen 720 to minimize the size of the balloon catheter 714. Since the catheter 714 does not track over a conventional guidewire, the catheter 714 also does not have a guidewire lumen or other structure to track over a guidewire which further reduces the size of the balloon catheter 714. The balloon catheter 714 also preferably has no distal opening so that the catheter 714 has a smooth, atraumatic tip which can be advanced through the obstruction if necessary. Thus, the balloon catheter 714 of the present invention provides advantages over conventional balloon catheters which track over guidewires.

The balloon catheter 714 is preferably sized and configured to provide a space 723 between the catheters 714, 500 so that the lumen 502 of catheter 500 may be used while the balloon catheter 714 is positioned therein. The balloon catheter 714 may generally have the tapered shape within the range of shapes of the catheters 500 so that the balloon catheter 714 essentially conforms to the shape of the lumen of the catheter 500. Such a configuration facilitates advancement of the balloon catheter 714 through the catheter 500. The distal portion of the catheter has a cross-sectional area of no more than 1.5 mm2 more preferably no more than 1.0 mm2 over a distal portion 724 of the catheter 714. The distal portion 724 preferably extends at least 5 cm and more preferably at least 10 cm from a distal end 726. The maximum outer dimension of the catheter 714 over the distal portion 724 may also be no more than 1.2 mm, 0.8 mm, 0.75 mm and most preferably no more than 0.65 mm in diameter.

Figure 20:
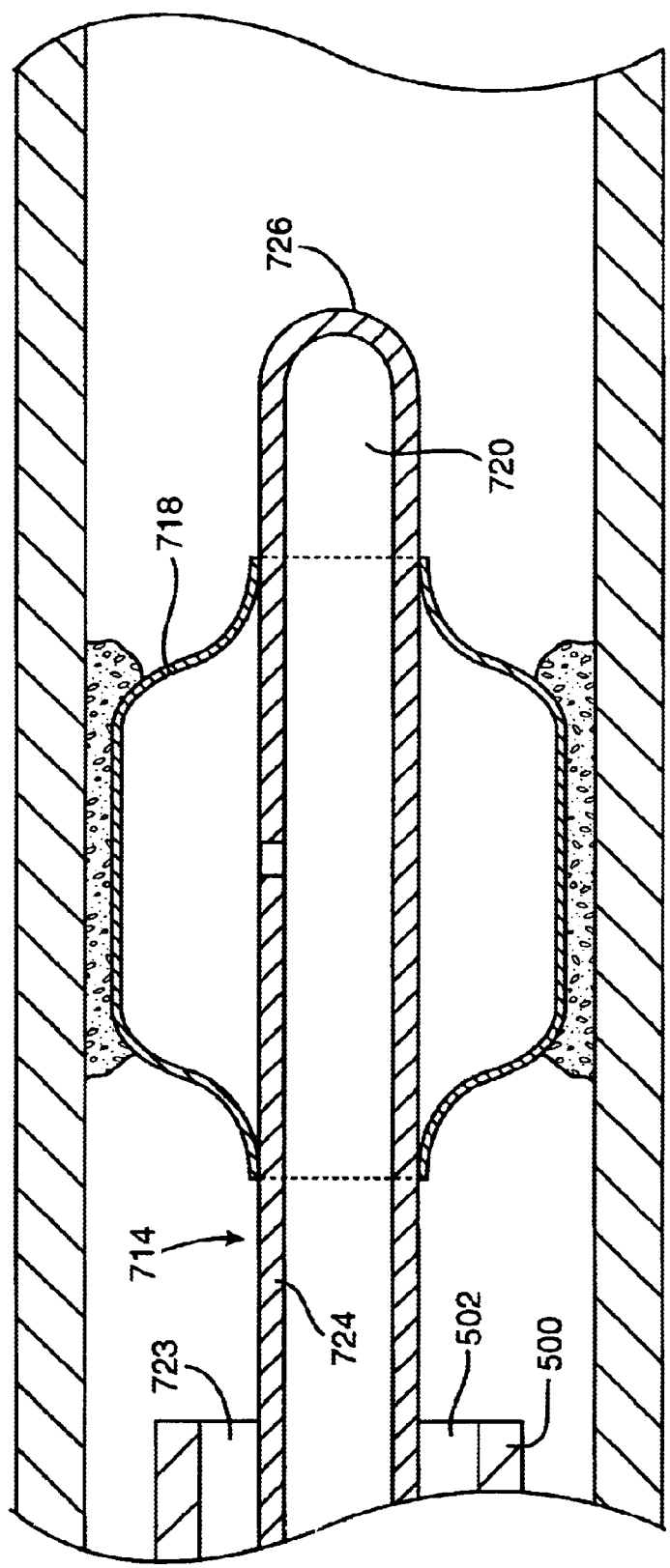
FIG. 20 shows a balloon catheter displacing an obstruction in a cerebral artery.
Figure 21:
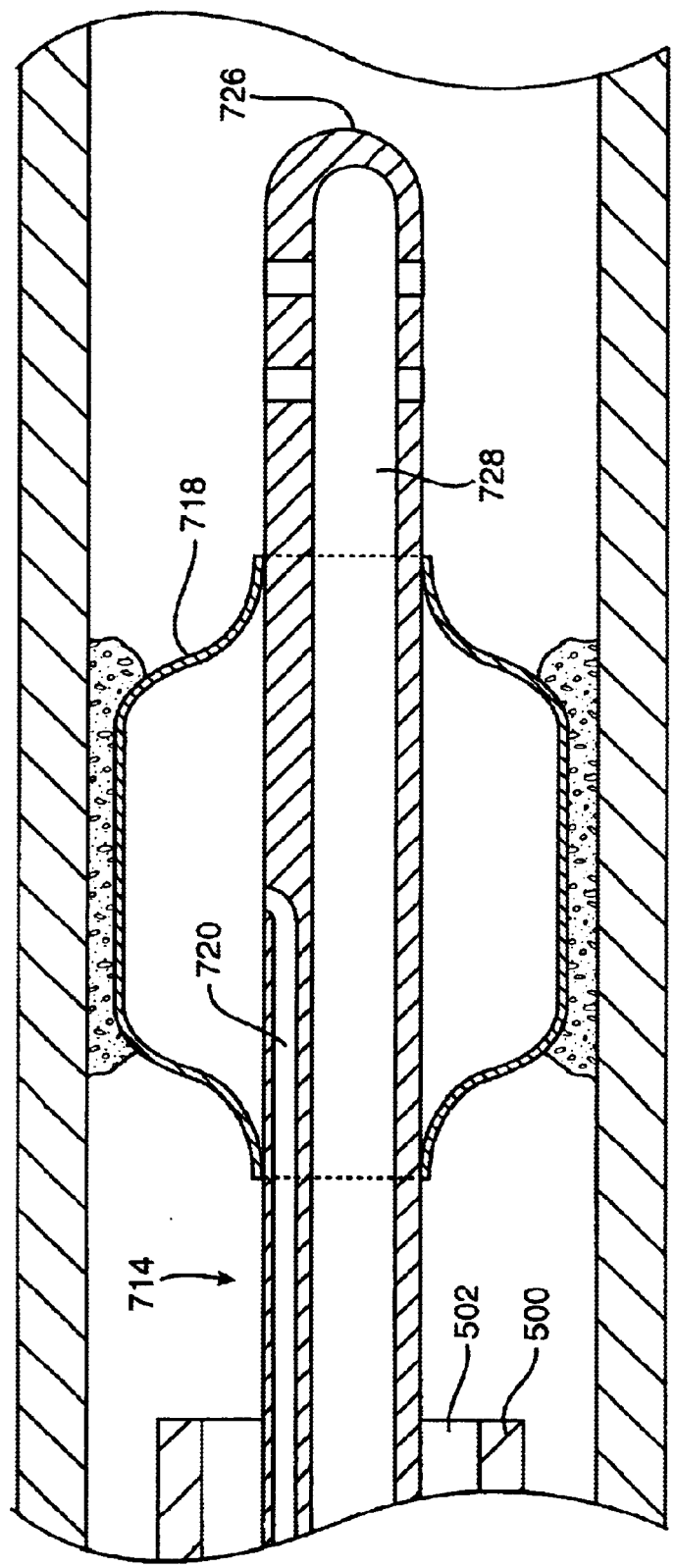
FIG. 21 shows another balloon catheter having a second lumen.

In another preferred method of the present invention, the catheter 500 is advanced through the obstruction to infuse oxygenated medium into the ischemic bed as described above. When the ischemic bed has been adequately perfused at the desired rates and pressures, the catheter 500 may be withdrawn through the obstruction. During withdrawal of the catheter, the lumen 502 may be coupled to the vacuum source 526 to capture emboli (FIG. 19). The balloon 718 may be positioned to lie within the obstruction as the catheter 500 is withdrawn, it may be advanced by itself through the obstruction after withdrawal of the catheter, or may be pulled back to lie within the obstruction by advancing the balloon beyond the obstruction within the catheter 500 before withdrawing the catheter 500. Once the balloon 718 is positioned within the obstruction, the balloon 718 is inflated to displace the obstruction as shown in FIG. 20. The lumen 502 may also be used to vent blood and thereby suction emboli while inflating the balloon 718. Although the catheter 714 preferably has only the inflation lumen 722, the catheter 714 may also have an infusion lumen 728 as shown in FIG. 21. The infusion lumen 728 is coupled to the system of FIG. 7 or 14 to infuse oxygenated medium and other fluids distal to the obstruction as described above, but the catheter 714 is otherwise used in the same manner as catheter 714.

Figure 22:
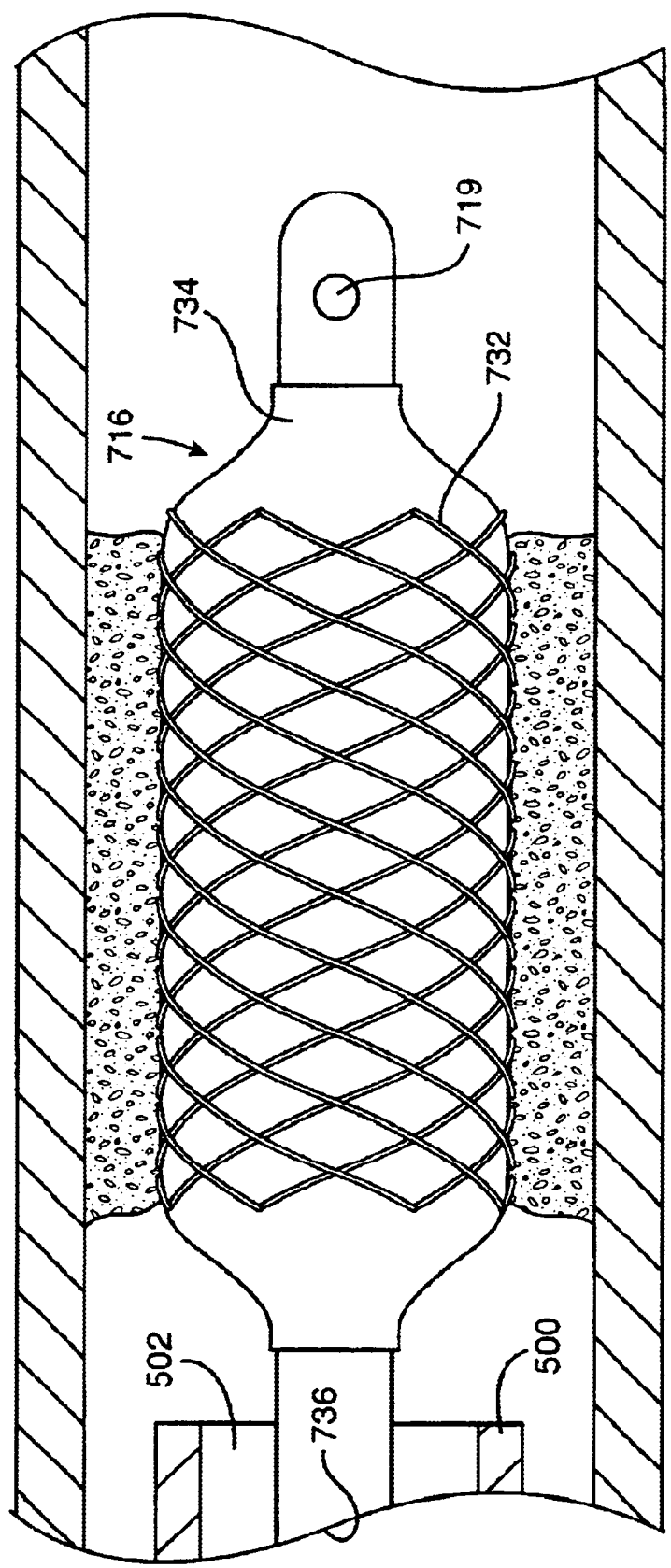
FIG. 22 shows a stent displacing an obstruction in a cerebral artery.
Figure 23:
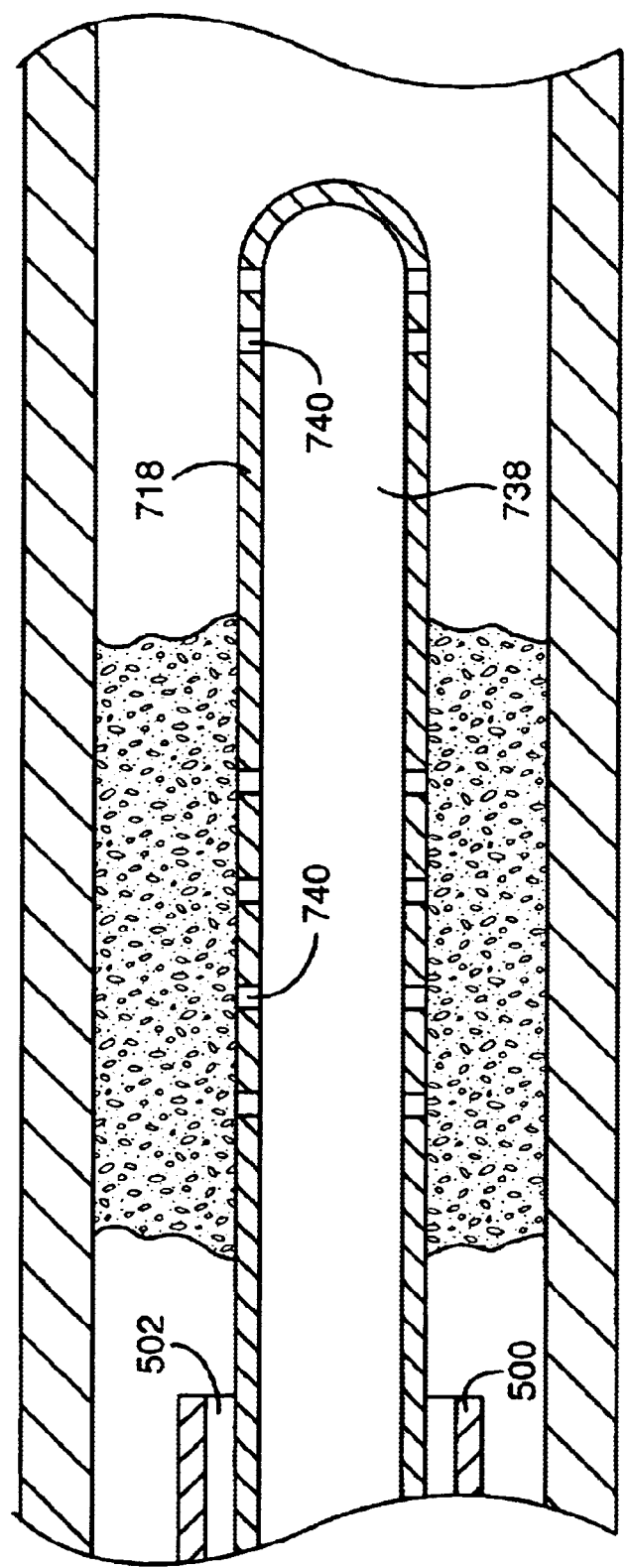
FIG. 23 shows a perfusion catheter for removing the obstruction.

Referring to FIG. 22, another system is shown which is similar to the system of FIG. 19 except that the stent catheter 716 is used instead of the balloon catheter 714. The stent catheter 716 is used in substantially the same manner as the balloon catheter 714 in that a stent 732 displaces the obstruction. The stent 732 is mounted to a balloon 734 having a lumen 736 coupled to the inflation source 722. The inflation lumen 736 is preferably sized like the lumen 728 and the preferred dimensions of the stent catheter 716 are the same as described above for the balloon catheter 714. The stent catheter 716 offers the same advantages as the balloon catheter 714 in that the stent catheter 716 does not require a guidewire lumen or other structure to track over a conventional guidewire. The stent 732 may be a suitable conventional stent 732 mounted to the catheter 716 of the present invention. The stent catheter 716 may also have a perfusion lumen and outlet 719, which may be a number of outlets or sideholes, for perfusing fluids as described above.

Referring to FIG. 23, the catheter 712 may also be the perfusion catheter 718 which passes through the catheter 500. The perfusion catheter 718 has a lumen 738 coupled to a source of solution 740 which is used to remove or dissolve the obstruction (FIG. 19). The perfusion catheter 718 is advanced through the catheter 500 so that openings 740 are positioned in or near the obstruction. The openings 740 may be at the distal end or spaced from the distal end. The catheter 500 is then withdrawn through the obstruction while venting through the lumen 738 with the vacuum source 526 to remove emboli. After the catheter 500 has been withdrawn, the solution is delivered through the perfusion catheter 718 and the dissolved obstruction can be withdrawn through the lumen 502 in the catheter 500 using the vacuum source 526. The catheter 500 and perfusion catheter 718 are both coupled to the system of FIG. 7 or 14 for periodic infusion of the oxygenated medium as necessary. The lumen 738 preferably has a cross-sectional area of no more than 1.54 mm2 and more preferably no more than 0.3 mm2, and most preferably no more than 0.19 mm2 along the distal portion of at least 5 cm. The maximum outer dimension of the catheter along the distal portion is preferably no more than 1.4 mm and more preferably no more than 0.95 mm and most preferably no more than 0.50 mm so that the lumen of the catheter 500 may still be used to suction the dissolved obstruction with the perfusion catheter 718 contained therein.

Although it is preferred to pass the catheters 714, 716, 718 directly through the catheter 500 thereby obviating the need to track over a guidewire, the catheters 714, 716, 718 may also be advanced over a guidewire which is advanced through the vasculature within the lumen 502 of catheter 500. Conventional guidewires are typically 0.014 inch to 0.018 inch in diameter and constructed to be flexible enough to reach the distal regions of the cerebral vasculature described above. After the guidewire has reached the desired location, a catheter can be advanced over the guidewire. At this point in the procedure, the guidewire must be rigid, rather than flexible, so that the catheter tracks over the guidewire without displacing the guidewire itself.

The devices and methods of the present invention permit the use of relatively large guidewires for advancement of catheters through the cerebral vasculature. This system does not require the use of smaller, more flexible guidewires since the guidewire is advanced through the catheter 500 rather than independently. The system promotes significant stability beyond that provided by conventional guidewires. The guidewire and corresponding guidewire lumen size of the catheter 712 are preferably larger than 0.018 inch, at least 0.028 inch, or at least 0.035 inch. The catheter 500 may then be removed and the catheter 712 advanced over the large stable guidewire. The catheter 500, or another perfusion catheter described herein, and the catheter 712 and/or guidewire may be packaged together in a kit for practicing the method as shown in FIG. 9.

Figure 26:
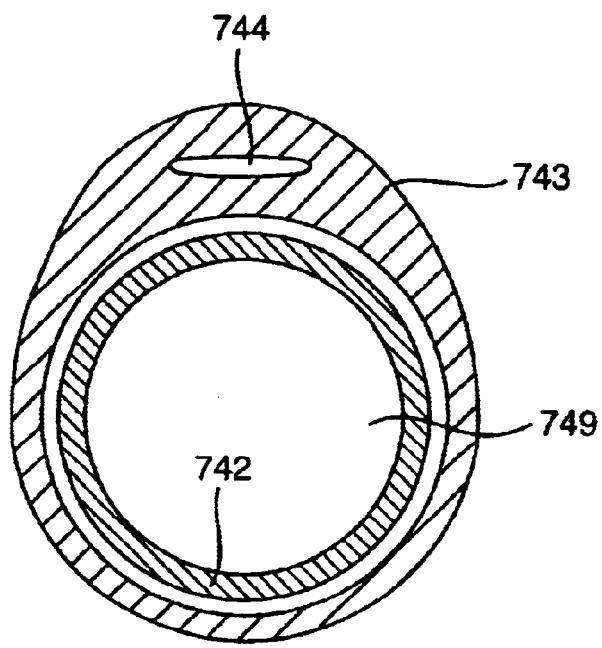
FIG. 26 is a cross-sectional view of the distal end of the catheters of FIGS. 23 and 24 with a lumen in a relaxed state.
Figure 27:
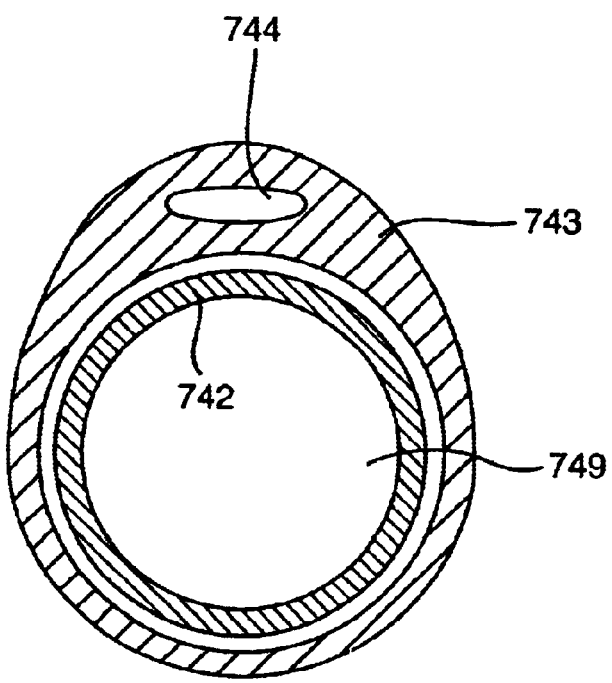
FIG. 27 is a cross-sectional view of the catheters of FIG. 23 with the lumen expanded.

Referring to FIG. 24, yet another system 740 for treating an obstruction in the cerebral vasculature is shown. The system 740 includes a first catheter 742 which passes through a second catheter 743. The first catheter 742 is coupled to the system of FIG. 7 or 14 for infusion of fluids in the manner described above. The second catheter 743 is coupled to a source of inflation fluid 744 for inflating a balloon 745. The system 740 is similar to the systems described above in that the first catheter 742 infuses the oxygenated medium while the balloon 745 displaces the obstruction. The first and second catheters 742, 743 are both tapered with the first catheter 742 positioned within the second catheter 743 with a close tolerance fit to reduce the overall size of the system. The catheters 742, 743 preferably have dimensions of the tapered catheters described above. Referring to FIGS. 24 and 25, the first catheter 742 may have a coiled tip 748 similar to a guidewire or may have a tubular shape similar to a catheter. Referring to FIGS. 26 and 27, the first catheter 742 has a lumen 749 which is coupled to the system of FIG. 7 or 14. An inflation lumen 744 may have a smaller cross-sectional size (FIG. 26) in a deflated position state relative to an inflated state (FIG. 27).

Another preferred method of the invention is now described with reference to FIG. 24. The second catheter 743 is advanced over a conventional guidewire (not shown) to a position within or near the obstruction. The guidewire is then removed and the first catheter 742 is introduced through the second catheter 743. The first catheter 742 is then advanced through the obstruction together with the second catheter 743 or by itself. Oxygenated medium is then delivered in the manner described above. After infusing the oxygenated medium for the desired time at the desired rates and pressures, the balloon 745 on the second catheter 743 is inflated to displace the obstruction. The balloon 745 may also be used to isolate the ischemic region from normal arterial flow.

Figure 28:
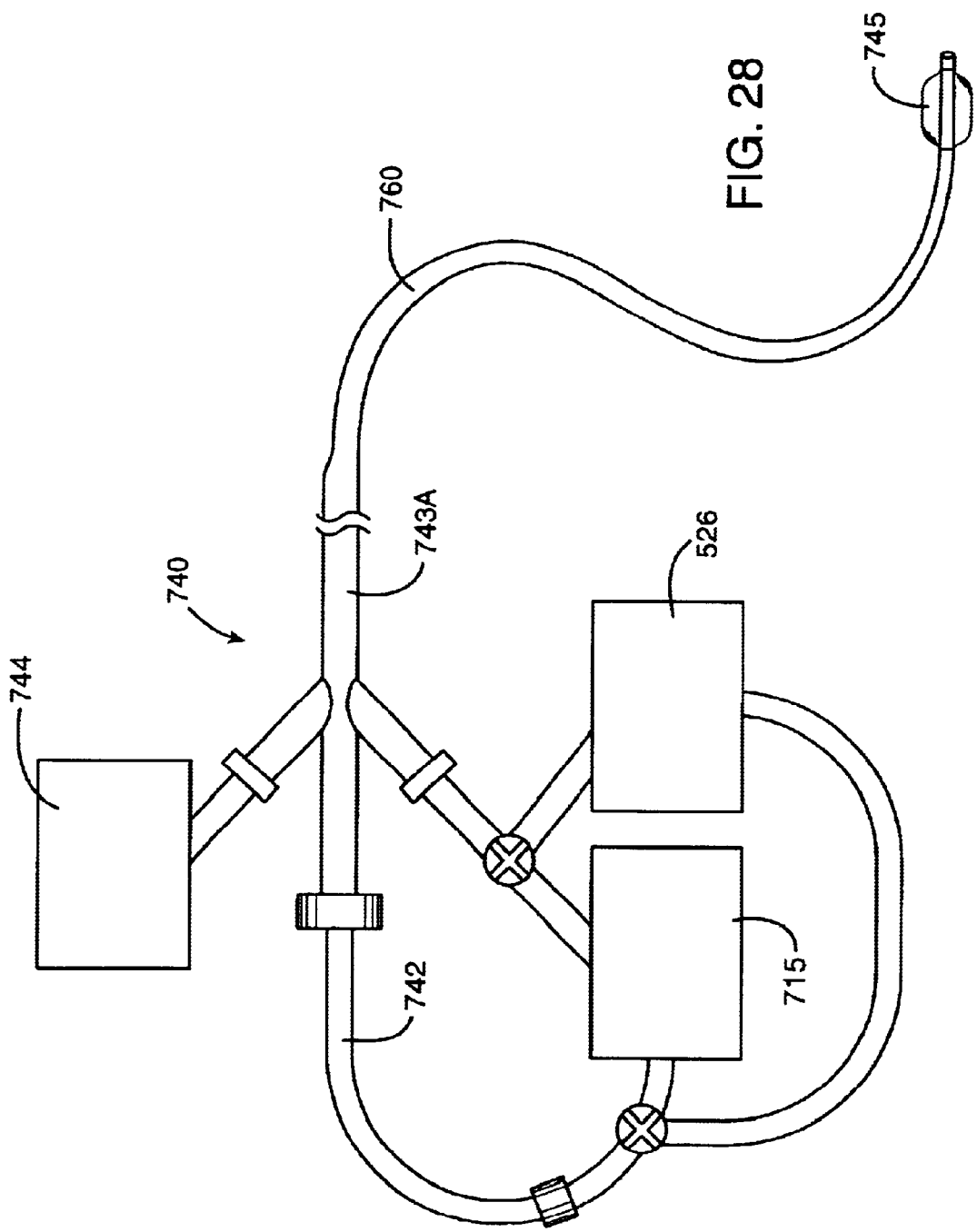
FIG. 28 is shows the system of FIG. 24 with an alternative second catheter having an expandable lumen.
Figure 29:
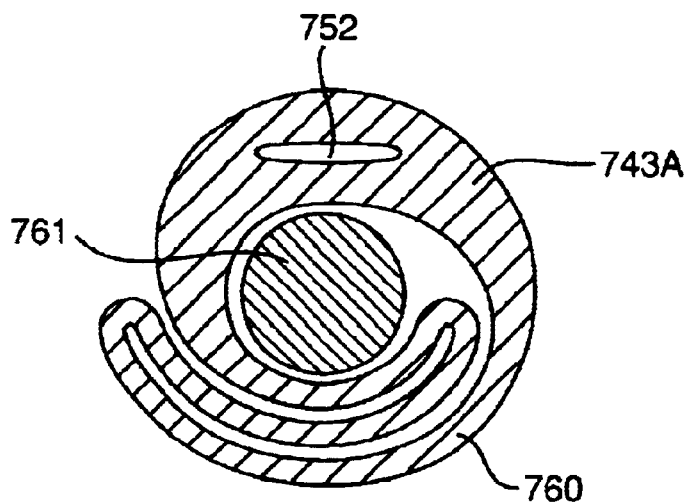
FIG. 29 shows the catheter of FIG. 29 having an expandable sidewall in a collapsed condition.
Figure 30:
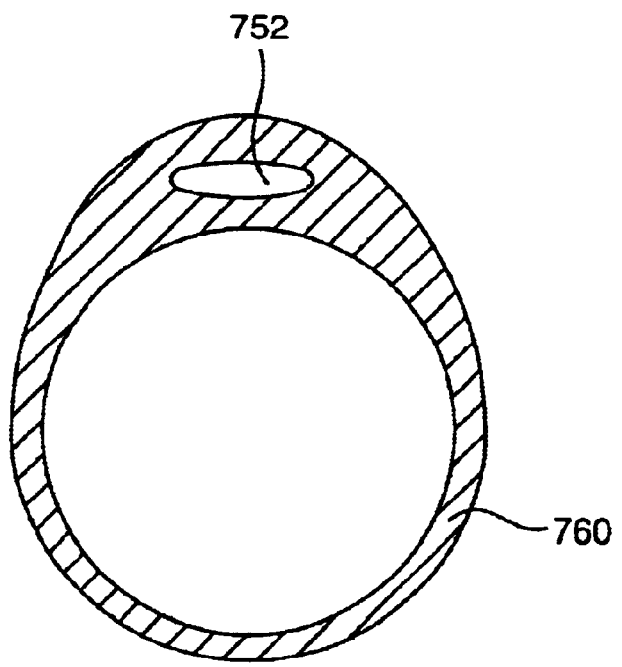
FIG. 30 shows the expandable sidewall in an expanded position.

Referring to FIGS. 28–30, an alternative second catheter 743A is shown which may be used in the same manner as second catheter 743 of FIGS. 24–27. The second catheter 743A has an expandable sidewall 760 which is folded or wrapped in a collapsed position and advanced over a guidewire 761 as shown in FIG. 29. The sidewall 760 provides a small profile when advanced through the vasculature and a large capacity for use in delivering fluids or other catheters as described above. The sidewall 760 preferably reduces the maximum outer dimension of the catheter along a portion by at least 25% while retaining the overall dimensions of the catheter 500 when in the expanded configuration. An inflation lumen 752 is coupled to the balloon 745 for inflating the balloon 745. The sidewall 760 may be made of any suitable material and is preferably a thermoplastic material having a wall thickness of no more than 0.38 mm and preferably no more than 0.25 mm. The sidewall 760 may be used with any of the other catheters described herein and is particularly advantageous for the catheters 10, 400, 500, 600. The sidewall 760 may take other forms without departing from the scope of the invention.

The second catheter 743A is advanced over the guidewire 761 with the sidewall 760 in the collapsed condition. When the balloon 745 is positioned proximate to the obstruction, the first catheter 742 is advanced through the catheter 743A. The sidewall 760 is expanded by the first catheter 742 to the expanded position of FIG. 24. The sheath 760 may also be expanded by an obturator or the like before introduction of the catheter 742. The first and second catheters 742, 743A may be then used in any manner described above.

Figure 31:
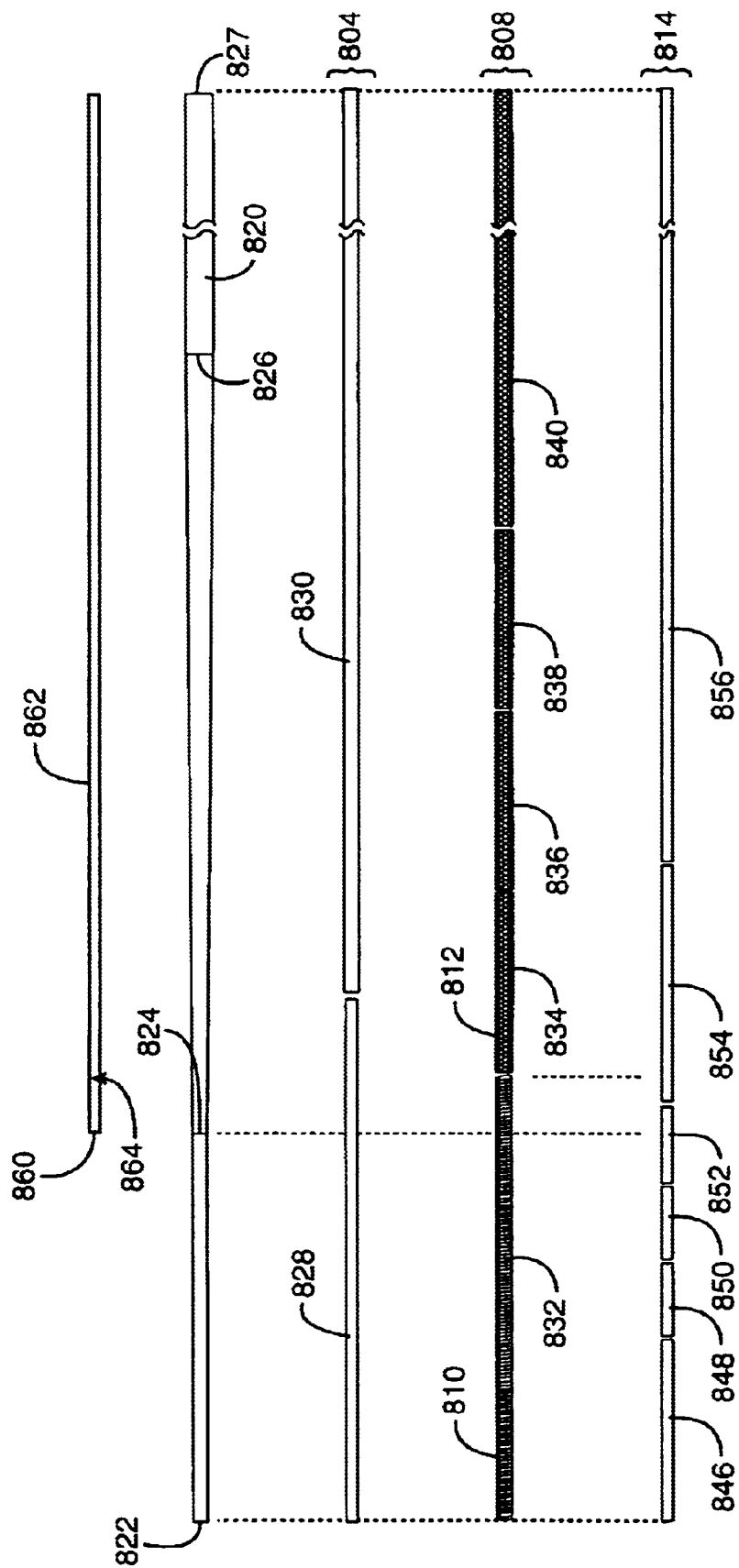
FIG. 31 is an exploded view showing a method of constructing an interventional device.

The devices 10, 400, 500, 600 described above may be manufactured in any suitable conventional manner. Although conventional methods may be used to manufacture the devices described above, a preferred method of constructing the devices is now described below in connection with FIGS. 31–34. Referring to FIG. 31, an exploded view of a preferred construction of an intravascular device 802 is shown. The intravascular device 802 may be used in any manner described above and the discussion above is incorporated here. For example, the device 802 may be used to deliver oxygenated media to a previously ischemic region or to deliver other interventional devices. The intravascular device 802 may also be used in other parts of the vascular system without departing from the scope of the invention.

The basic construction and method of constructing the device 802 are now described in general terms and more specific details are given below. A liner 804 is mounted to a mandrel 806. The liner 804 forms the inner lining of a lumen 807 extending through the device 802. A reinforcing layer 808 is positioned over the liner 804. The reinforcing layer 808 is preferably wound or braided onto the liner 804 and may be a coil 810 or a woven or braided structure 812. A jacket 814 is then positioned over the reinforcing layer 808.

Figure 33:
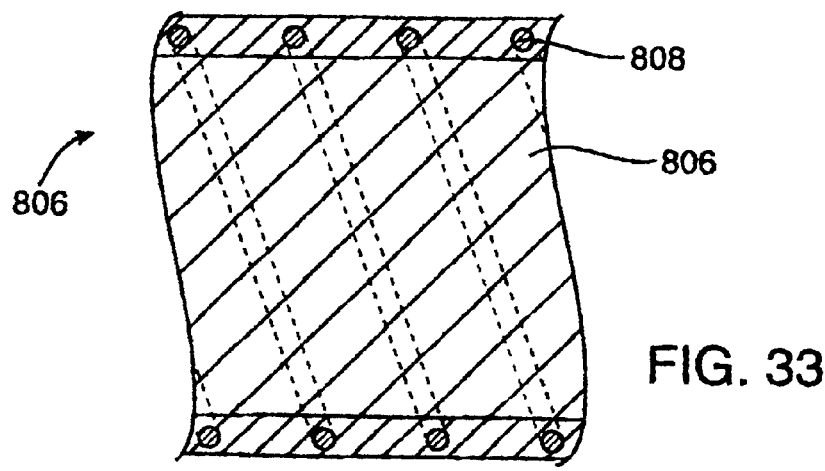
FIG. 33 is a cross-sectional view of the device of FIG. 32 after heating to fuse the layers together to form an integrated device.

A shrink tube 815 is then positioned over the jacket 814 and heated to melt and fuse the layers 804, 814 together to form an integrated structure as shown in FIG. 33. Although the preferred construction includes only the liner 804, reinforcing layer 808 and jacket 814, the device 802 may include other layers and may have coatings, such as a heparin-type or hydrophilic coating, which cover the inner and/or outer surfaces without departing from the scope of the invention.

The mandrel 806 generally defines the interior geometry of the lumen 807 and preferred dimensions of the lumens described above are applicable here. The mandrel 806 has a proximal portion 816, an intermediate portion 818, and a distal portion 820. The distal portion 820 preferably has a constant inner diameter of 0.030–0.050 inch, more preferably 0.040–0.050 inch and most preferably about 0.046 inch. The distal portion preferably extends at least 10 cm and more preferably at least 15 cm from a distal end 822. The intermediate portion 818 tapers up from 0.046 to at least 0.070 inch, more preferably at least 0.080 inch and most preferably about 0.085 inch and extends 30 cm between a first transition 824 and a second transition 826. The proximal portion 816 preferably has a constant,inner diameter of 0.070 to 0.100 inch, more preferably 0.080 to 0.090 inch and preferably about 0.085 inch for a length of at least 80 cm and more preferably about 105 cm to a proximal end 827. Although the lumen 807 has the dimensions described above for the mandrel 806, the lumen 806 may also be within the lumen size ranges given above in connection with any of the embodiments described above.

The liner 804 has a distal portion 828 which is made of expanded PTFE and a proximal portion 830 which is made of etched PTFE. An advantage of using expanded PTFE is that the distal portion 828 has a flexibility which is greater than with etched PTFE. Another advantage of the liner 804 is that the two different PTFE materials provide differing column strength and tip deflection for the proximal and distal sections 830, 828. The distal portion 828 has the expanded PTFE to provide flexibility to navigate small and tortuous vessels. The stiffer proximal portion 830 has the etched PTFE liner which provides pushability and column strength for advancement of the device 802 through the vascular system. The distal portion 828 preferably extends 15–25 cm and more preferably about 21 cm from the distal end 822 but may extend the length of the device. The proximal portion 830 preferably overlaps the distal portion 828 for about 0.3 cm with the distal portion 828 positioned inside the proximal portion 830 to reduce pressure drop at the transition of the proximal and distal portions 828, 830. A suitable material for the distal portion 828 of the liner 804 is expanded PTFE having a wall thickness of 0.002 inch and a diameter of 0.037 inch. The expanded PTFE is stretched onto the mandrel which has a diameter of 0.046 inch. A suitable material for the proximal portion 830 of the liner 804 is etched PTFE having a wall thickness of 0.002 inch and a diameter of 0.093 which is shrunk onto the mandrel which has a diameter of 0.046–0.085 inch. The etched PTFE is shrunk onto the mandrel with heat and tension. The expanded PTFE preferably has an internodal spacing of 10–120 microns, more preferably 10–60 microns and most preferably about 20–30 microns. The proximal and distal portions 830, 828 may, of course, both be made of the same material, such as etched PTFE or expanded PTFE, without departing from the scope of other aspects of the present invention.

The reinforcing layer 808 has a number of sections, preferably at least four and more preferably at least five sections, to vary the flexibility along the device 802. The high variability permits use of the device 802 without a guiding catheter as described above although a guide catheter may be used without departing from the scope of the invention. The reinforcing layer 808 has a first section 832, a second section 834, a third section 836, a fourth section 838 and a fifth section 840. The first section 832 is a coil reinforcing element 842 extending along the distal portion 820 of the mandrel 806 just beyond the transition 824 to the tapered, intermediate portion 818, preferably about 19 cm from the distal end 822 and 4 cm beyond the transition 824. The coil 842 is preferably 0.003 inch diameter stainless steel wire wound to have a centerline spacing of about 0.012 inch. The second, third, fourth and fifth sections 834, 836, 838, 840 are preferably braided 0.003 inch diameter stainless steel wire. The second, third, fourth and fifth sections 834, 836, 838, 840 are shown separated for clarity but are preferably continuously wound with the pic being automatically varied during winding. The second section 834 overlaps the first section for about 1 cm and begins about 18 cm from the distal end. The second section 834 has 70 pics, the third section 836 has 60 pics, the fourth section 838 has 50 pics and the fifth section 840 has 30 pics. The second section 834 extends 7 cm, the third section 836 extends 7 cm, the fourth section 838 extends 7 cm through the transition 826, and the fifth section extends to the proximal end 827. Although the reinforcing layer has the specific characteristics described above, the sections may vary as follows. The second section 834 preferably has a pic which is at least 15 more, and more preferably at least 20 more, than the fourth section 838. The second section 834 is preferably separated from the fourth section 838 by no more than 15 cm and preferably no more than 10 cm. The first section preferably has a pic which is at least 30 pics more than the fifth section 840 with the first section separated from the fifth section by no more than 20 cm and more preferably no more than 15 cm. Although the reinforcing layer 808 has the preferred characteristics described above, the reinforcing layer 808 may be any suitable structure and may be entirely coil, braid, or weave. The reinforcing layer 808 may also be made of any suitable material such as shape memory alloy or polymer.

The jacket 814 preferably includes a number of sections, preferably at least four, more preferably at least five and most preferably at least six sections, which also enhance variation in flexibility. The high variation in flexibility provides good flexibility at the distal portion while providing column strength at the proximal portion to advance the device 802 and prevent kinking. The high variability in the jacket 814 also provides a smooth transition in stiffness between the distal and proximal sections. The jacket 814 has first, second, third, fourth, fifth and sixth liner sections 846, 848, 850, 852, 854, 856 which are mounted next to one another on the mandrel 806. The flexural modulus of the jacket preferably increases at least 25, more preferably at least 40 times, and most preferably about 55 times from the first section 846 to the sixth section 856. Specifically, the jacket flexural modulus increases from 2000 psi at the first section 846 to 110,000 at the sixth section 856. The flexural modulus of the jacket 814 also increases at least 10 times, more preferably at least 15 times and most preferably about 17.5 times over a 10 cm distance from the second section 848 to the fifth section 854.

The jacket sections also preferably increases in durometer towards the proximal end. The durometers of the sections are as follows; the first section 846 is 25 D, the second section 848 is 35 D, the third section 850 is 40 D, the fourth section 852 is 55 D, the fifth section 854 is 63 D, and the sixth section 856 is 72 D. The sections extend for the following lengths, the first section 846 extends 7 cm from the distal end 822, the second section 848 extends 3 cm, the third section 850 extends 3 cm, the fourth section 852 extends 3 cm through the transition 824 to the intermediate portion 818, the fifth section 854 extends 9 cm along the intermediate portion 818, and the sixth section 856 extends 125 cm. The first, second, third and fourth sections 846, 848, 850, 852 have an inner diameter of 0.080 inch. The fifth section 854, which extends through the tapered, intermediate section 818, has a diameter of about 0.095 inch and the sixth section 856 has a diameter of 0.105 inch. All jackets sections are preferably made of pellethane, polyurethane or the like. The dimensions may, of course, be modified without departing from the scope of the invention.

Figure 32:
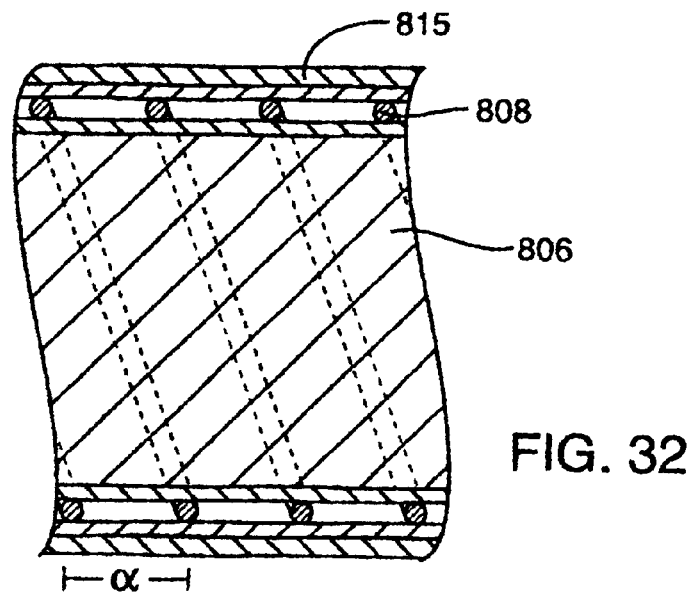
FIG. 32 is a cross-sectional view showing the method of constructing the interventional device of FIG. 31.

As mentioned above, the liner 804, reinforcing elements 808 and jacket 814 are mounted on the mandrel 806. Other layers may be positioned over the jacket 814 but in the preferred embodiment the jacket 814 forms the outer layer of the device 802. The shrink tube 815 is positioned over the jacket 814 as shown in FIG. 32 and the entire structure is heated to form the integrated structure 860 of FIG. 33. The resulting wall thickness of the device 802 is about 0.005 inch, preferably 0.004 to 0.007 inch, along the distal portion 820 of the liner 804. The wall thickness of the proximal portion 816 tapers up from 0.005 inch to 0.015 inch from the end of the first section of the reinforcing layer to the proximal end. Although the preferred embodiment provides specific jacket sections and reinforcement construction, the flexibility of the device may be provided by other combinations of jacket 814 and reinforcing layer without departing from the scope of the invention.

The gradual change in stiffness also provides an advantage when advancing the catheter through small, tortuous vessels. Conventional microcatheters must be advanced over a guidewire since the microcatheters do not have sufficient column strength to be advanced without the aid of a guidewire. The catheter of the present invention can be advanced through the vasculature without the aid of a guidewire although a guidewire may be used when needed. The change in stiffness helps to resists buckling at the proximal portion while retaining sufficient flexibility at the distal portion to navigate small and tortuous vessels. Conventional microcatheters have low column strength at the distal portion which requires the microcatheters to be advanced over a guidewire. The guidewire generally has an outer diameter within 0.005 inch of the inner diameter of the lumen so that the guidewire supports the distal portion to prevent kinking. The distal portion of the present catheter has sufficient column strength to be advanced without a guidewire.

In a specific application of the present invention, the catheter is advanced to the common carotid artery over a conventional guidewire such as an 0.035 inch diameter guidewire. The distal portion is then advanced without the aid of a guidewire into intracranial vessels having a size of 4–5 mm and even 3 mm in diameter. Stated another way, the catheter of the present invention may be used to access vessels such as the middle or anterior cerebral arteries and the vertebral, basilar and posterior cerebral arteries when accessing the cerebral vasculature.

The catheter of the present invention also has a high change in flexibility from a proximal portion to a distal portion. Specifically, the proximal section is at least 20, 40, 60 or even 75 times stiffer than the distal portion of the catheter. The distal portion preferably extends at least 5, more preferably at least 10, and more preferably at least 15 cm from the distal end while the proximal portion extends to within 40, 35 and most preferably to within 30 cm from the distal end or closer. The high change in stiffness permits the proximal portion to be rigid enough to prevent buckling and kinking while the distal portion is flexible to pass through tortuous vessels.

Figure 34:
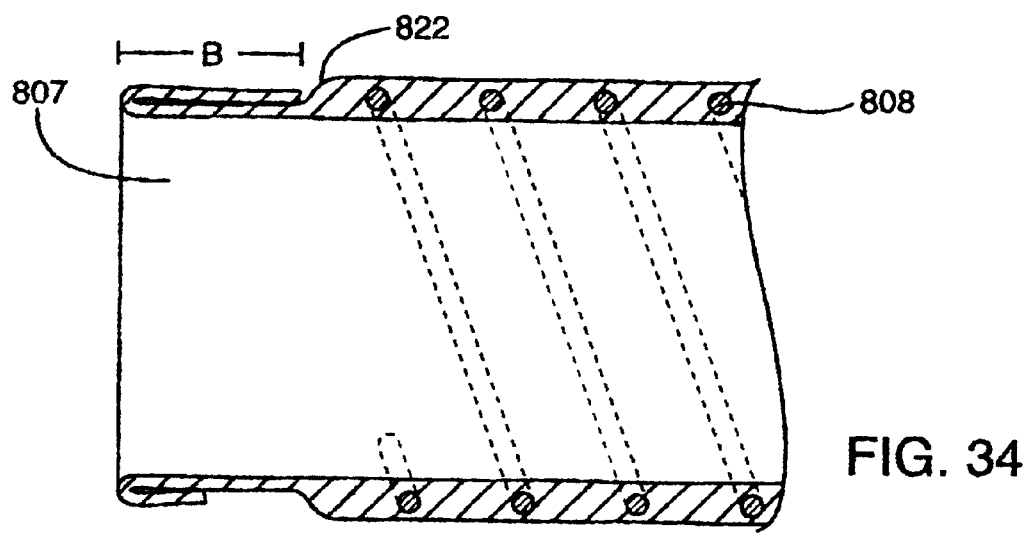
FIG. 34 shows the distal end of the device with the liner having an inverted portion at the distal end.

Referring to FIG. 34, the distal end 822 of the device is shown with the distal portion 828 of the liner 804 extending beyond the reinforcing layer 808 and the jacket 814 after heating to form the integrated structure. The end of the liner 804 is everted to form a soft, atraumatic distal end. The end of the liner 804 is everted for a length of at least 0.5 mm, more preferably 1–2 mm, and preferably 2 mm to form the soft tip. Use of the expanded PTFE material for the distal portion 828 provides a soft tip which helps to navigate the device through small and tortuous vessels. The proximal end is then attached to the necessary connectors and hemostasis valves so that the device 802 forms all or part of the intravascular device such as the devices 10, 400, 500, 600 described above. The device 802 may, of course, be used for other procedures and in other parts of the body.

Figure 36:
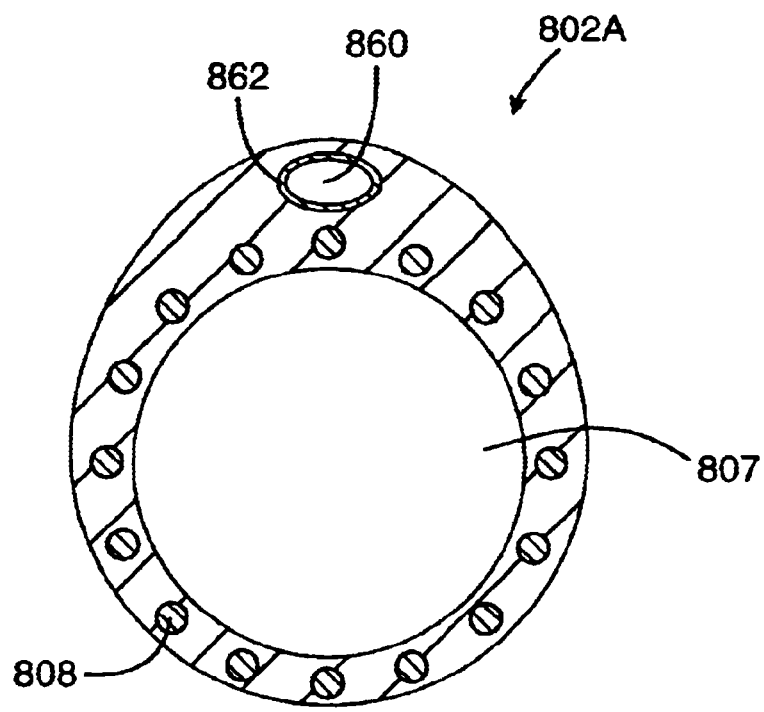
FIG. 36 is another cross-sectional view of the device of FIG. 35.
Figure 35:
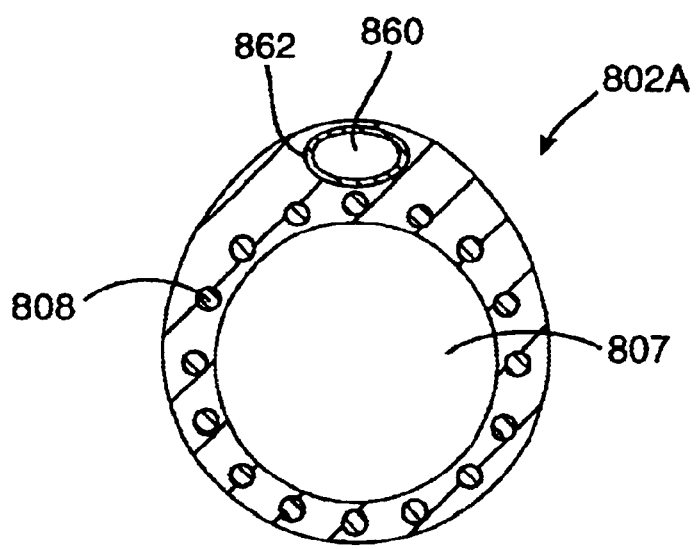
FIG. 35 is a cross-sectional view of another device.

Referring to FIGS. 31, 35 and 36, another device 802A is shown which has the lumen 807 and an additional lumen 860 wherein the same or similar reference numbers refer to the same or similar structure. FIG. 35 shows a cross-sectional view along the distal portion and FIG. 36 is a cross-sectional view of the device 802A along the proximal portion. The device 802A is constructed in substantially the same manner as the device 802 and the discussion above is equally applicable here. The lumen 860 is formed by a tube 862 which is essentially bonded to the device 802 in the manner described below. The lumen 860 preferably has a cross-sectional area of 0.050 to 0.620 mm2 and more preferably 0.200 to 0.400 mm2.

The tube 862 is preferably a polyimide tube having an inner diameter of 0.020–0.035 inch, preferably about 0.026 inch, with a wall thickness of 0.001 to 0.002 inch. Of course, any other suitable material and size may be used. The tube 862 has a length of about 134 cm with an opening 864 positioned 5–26 cm, more preferably 10–26 cm, and most preferably about 18 cm from the distal end of the device 802A. The opening 864 may also be closer to the distal end without departing from the scope of the invention. The opening 864 is preferably positioned along the tapered portion of the device 802A but may also be at the constant diameter distal portion. The opening 864 is shown formed in the tube 862 in FIG. 31 for clarity, however, the opening 864 is preferably formed after forming the integrated structure of FIGS. 35 and 36 as described below.

The tube 862 is preferably rolled through a die to create an oblong cross-sectional shape. The tube 862 is then positioned over the jacket 814 and is covered by the shrink tube as described above. The jacket 814 is positioned over the reinforcing layer 808 and liner 804 in the manner described above. The tube 862 is preferably coated with a polymer, such as polyurethane having a thickness of 0.002–0.003 inch, which fuses with the jacket 814 when melted. The tube 862 may melt and fuse with the jacket 814 or may be designed to remain solid during heating as shown in FIGS. 35 and 36. The end of the tube 862 is crimped to close the distal end and the opening 864 is formed after forming the integrated structure of FIG. 35. A teflon-coated mandrel may be positioned in the tube 862 to hold the tube 862 open during heating and melting.

The device 802A may be used in any manner described above and the discussion above is equally applicable here. Furthermore, the device 860A may have the features of the other multi-lumen devices described herein and the discussion of the various dimensions and preferred uses described herein are also applicable here. For example, the device 802A may be used to deliver an oxygenated medium to a previously ischemic region in the manner described above. The lumen 860 may be used to deliver thrombolytic, anticoagulant and/or anti-restenotic agents. The lumen 860 may also be used to deliver contrast or to measure pressure.

While the above is a complete description of the preferred embodiments, various alternatives, modifications, and equivalents may be used. The terms first liner, second liner . . . or first portion, second portion are used for ease of reference in the drawings and figures, however, these terms may refer to other sections or portions without departing from the scope of the invention. Thus, when the claims recite that a first liner section has a preferred durometer change with respect to a third liner section, the first and third sections in the claims may actually refer to a second and fourth liner sections or to fourth and sixth liner sections without departing from the scope of the claims. Therefore, the above description should not be taken as limiting the scope of the invention which is defined by the appended claims.

What is claimed is:

1. A method of forming an intravascular device, comprising the steps of:

mounting an expanded PTFE liner over a first mandrel portion and an etched PTFE liner over a second mandrel portion;

placing a reinforcing layer over the expanded and etched PTFE liners after the mounting step; and applying a jacket layer over the reinforcing layer.

2. The method of claim 1, further comprising the steps of:

covering the jacket layer, the reinforcing layer and the expanded PTFE liner with a shrink tube;

fusing the jacket layer to the expanded PTFE liner to form an integrated structure; and removing the shrink tube after the fusing step.

3. The method of claim 1, wherein:

the applying step is carried out by positioning a tube of material over the reinforcing layer.

4. The method of claim 1, wherein:

the applying step is carried out with the jacket layer having a first jacket section and a second jacket section, the first jacket section being positioned over the expanded PTFE liner and the second jacket section being positioned over the etched PTFE liner, the first jacket section having a durometer which is at least 30 D less than the second jacket section.

5. The method of claim 4, wherein:

the applying step is carried out with the first jacket section having a durometer which is at least 40 D less than the second jacket section.

6. The method of claim 1, wherein:

the mounting step is carried out with the expanded PTFE liner having a porosity of 8–10 microns.

7. The method of claim 1, wherein:

the mounting step is carried out with the first and second mandrel portions being part of the same mandrel.

8. The method of claim 1, further comprising the step of:

inverting an end of the expanded PTFE liner at a distal end.

9. The method of claim 8, wherein:

the inverting step is carried out to form an inverted portion of the expanded PTFE liner which extends longitudinally at least 0.5 mm from a distal end of the reinforcing layer.

10. A method of forming an intravascular device, comprising the steps of:

providing a first mandrel portion and an expanded PTFE liner, the expanded PTFE liner being mounted on the first mandrel portion;

positioning a reinforcing layer over the expanded PTFE liner; applying a jacket layer over the reinforcing layer; and positioning an etched PTFE liner over a second mandrel portion;

the positioning step being carried out with the reinforcing layer being wound over the etched PTFE liner; and the applying step is carried out with the jacket layer being positioned over the reinforcing layer and the etched PTFE liner after the positioning step.

11. The method of claim 10, further comprising the steps of:

covering the jacket layer, the reinforcing layer and the expanded PTFE liner with a shrink tube;

fusing the jacket layer to the expanded PTFE liner to form an integrated structure; and structure; and removing the shrink tube after the fusing step.

12. The method of claim 10, wherein:

the applying step is carried out by positioning a tube of material over the reinforcing layer.

13. The method of claim 10, wherein:

the positioning step is carried out with the expanded PTFE liner having a porosity of 8–10 microns.

14. The method of claim 13, wherein:

the positioning step is carried out with the first and second mandrel portions being part of the same mandrel.

15. The method of claim 10, further comprising the step of:

inverting an end of the expanded PTFE liner at a distal end.

16. The method of claim 15, wherein:

the inverting step is carried out to form an inverted portion of the expanded PTFE liner which extends longitudinally at least 0.5 mm from a distal end of the reinforcing layer.

17. A method of forming an intravascular device, comprising the steps of:

providing a first mandrel portion and an expanded PTFE liner, the expanded PTFE liner being mounted on the fist mandrel portion;

positioning a reinforcing layer over the expanded PTFE liner;

applying a jacket layer over the reinforcing layer; and inverting an end of the expanded PTFE liner at a distal end.

18. The method of claim 17, further comprising the steps of:

positioning an etched PTFE liner over a second mandrel portion; and the positioning step is carried out with the reinforcing layer being wound over the etched PTFE liner; and the applying step is carried out with the jacket layer being positioned over the reinforcing layer and the etched PTFE liner after the positioning step.

19. The method of claim 18, wherein:

the applying step is carried out with the jacket layer having a first jacket section and a second jacket section, the first jacket section being positioned over the expanded PTFE liner and the second jacket section being positioned over the etched PTFE liner, the first jacket section having a durometer which is at least 30 D less than the second jacket section.

20. The method of claim 19, wherein:

the applying step is carried out with the first jacket section having a durometer which is at least 40 D less than the second jacket section.

* * * * *